US009629817B2

(12) United States Patent
Weiss

(10) Patent No.: US 9,629,817 B2
(45) Date of Patent: Apr. 25, 2017

(54) REDUCING MYOCARDIAL DAMAGE AND THE INCIDENCE OF ARRHYTHMIA ARISING FROM LOSS, REDUCTION OR INTERRUPTION IN CORONARY BLOOD FLOW

(76) Inventor: Steven Michael Weiss, Deakin (AU)

( * ) Notice: Subject to any disclaimer, the term of this patent is extended or adjusted under 35 U.S.C. 154(b) by 255 days.

(21) Appl. No.: 12/064,077

(22) PCT Filed: Aug. 24, 2006

(86) PCT No.: PCT/AU2006/001207
§ 371 (c)(1),
(2), (4) Date: Feb. 18, 2008

(87) PCT Pub. No.: WO2007/022568
PCT Pub. Date: Mar. 1, 2007

(65) Prior Publication Data
US 2008/0234339 A1      Sep. 25, 2008

(30) Foreign Application Priority Data

Aug. 25, 2005   (AU) .................................. 2005904615

(51) Int. Cl.
| | | |
|---|---|---|
| A61K 31/33 | (2006.01) |
| A61K 31/136 | (2006.01) |
| A61K 31/167 | (2006.01) |
| A61K 31/198 | (2006.01) |
| A61K 31/423 | (2006.01) |
| A61K 31/428 | (2006.01) |
| A61K 31/58 | (2006.01) |
| A61K 45/06 | (2006.01) |

(52) U.S. Cl.
CPC .......... *A61K 31/136* (2013.01); *A61K 31/167* (2013.01); *A61K 31/198* (2013.01); *A61K 31/423* (2013.01); *A61K 31/428* (2013.01); *A61K 31/58* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,800,226 A | 1/1989 | Dillon et al. | |
| 4,945,114 A | 7/1990 | Franke et al. | |
| 7,196,197 B2 | 3/2007 | Wang et al. | |
| 8,097,650 B2 * | 1/2012 | Feinmark et al. | 514/476 |
| 2005/0054695 A1 | 3/2005 | Ehring et al. | |

FOREIGN PATENT DOCUMENTS

| | | |
|---|---|---|
| AU | 2006284513 B2 | 3/2007 |
| WO | WO-00/66121 | 11/2000 |
| WO | WO-02/45705 A2 | 6/2002 |
| WO | WO-02/066413 A1 | 8/2002 |
| WO | WO 2004/056180 * 7/2004 | ............ A01N 1/02 |
| WO | WO-2005/075488 A1 | 8/2005 |

OTHER PUBLICATIONS www.wrongdiagnosis.com accessed online Feb. 2, 2010.*
Kanthasamy et al (JPET 288:1340-1348, 1999).*
Lu et al (Eur J Pharmacol 365:233-239, 1999).*
Grant (Am J Med 110:296-305, 2001).*
Duprat et al (Mol Pharmacol 57:906-912, 2000).*
Tian et al (Cardiovasc Res 61:256-267, 2004).*
Ju et al (Br J Pharmacol 107:311-316, 1992).*
Urbani et al (Eur J Neurosci 12:3567-3574, 2000; Abstract only).*
Ju et al (J Physiol 497:337-347, 1996).*
Belardinelli et al (Eur Heart J Supp 6(Suppl 1):13-17, 2004).*
McIntosh et al (J Neurotrauma 13:767-780, 1996—Abstract only).*
A. Sugiyama et al., "Antiischemic effects of CP-060S, an inhibitor of pathologically modified sodium channels, assessed in the canine experimental model of angina pectoris", *J. Cardiovasc Pharmacol.*, 33(1), pp. 70-77 (1999). (Abstract Only).
W. Thomsen et al., "Specific Binding of the Novel Na$^+$ Channel Blocker PD85,639 to the α Subunit of Rat Brain Na$^+$ Channels" *The American Society for Pharmacology and Experimental Therapeutics*, vol. 43, pp. 955-964 (1993).
N. Toriu et al., "Lomerizine, a Ca$^{2+}$ Channel Blocker, Reduces Glutamate-induced Neurotoxicity and Ischemia/Reperfusion Damage in Rat Retina", *Exp. Eye Res.*, vol. 70, pp. 475-484 (2000).
J.G. Van Emous et al., "The Role of the Na$^+$ Channel in the Accumulation of Intracellular Na$^+$ During Myocardial Ischemia: Consequences for Post-ischemic Recovery", *J. Mol. Cell Cardiol*, vol. 29, pp. 85-96 (1997).
ID Wijnberg et al., "Phenytoin sodium as a treatment for ventricular dysrhythmia in horses", *J. Vet. Intern Med.*, 18(3), pp. 350-353 (2004). (Abstract Only).
W.D. Yonekawa et al., "The effects of anticonvulsant agents on 4-aminopyridine induced epileptiform activity in rat hippocampus in vitro", *Epilepsy Research*, vol. 20, pp. 137-150 (1995).

(Continued)

*Primary Examiner* — Craig Ricci

(57) ABSTRACT

A method and pharmaceutical composition are disclosed for treating, ameliorating and/or preventing one or more myocardial disorders in a mammalian heart caused by a myocardial hypoxic event and/or a loss, reduction or interruption in coronary blood flow such as may happen during or after events such as a heart attack, cardiac surgery including coronary artery bypass graft, or coronary artery or myocardial reperfusion. The myocardial disorders include myocardial arrhythmias, myocardial damage and myocardial cell death, and the subsequent loss of haemodynamic function. The myocardial disorders could be in progress or suspected of being in progress at the time of treatment or could be anticipated disorders being treated prophylactically. The method involves the step of administering an effective amount of the composition. The composition comprises as its active ingredient one or more compounds having myocardial persistent sodium channel blocking activity. A preferred compound is riluzole or a salt or derivative thereof.

7 Claims, 5 Drawing Sheets

(56) References Cited

OTHER PUBLICATIONS

P.P. Neidhart et al., "A comparison of pipecuronium with pancuronium on haemodynamic variables and plasma catecholamines in coronary artery bypass patients", *Canadian Journal of Anaethesia*, 41(6), pp. 469-474 (1994).
M.J. O'Neill et al., "Effects of $Ca_{2+}$ and Na+ channel inhibitors in vitro and in global cerebral ischaemia in vivo", *European Journal of Pharmacology*, vol. 332, pp. 121-131 (1997).
I.M. Raman et al., "Inactivation and Recovery of Sodium Currents in Cerebellar Purkinje Neurons: Evidence for Two Mechanisms", *Biophysical Journal*, vol. 80, pp. 729-737 (2001).
I. Roufos et al., "A Structure—Activity Relationship Study of Novel Phenylacetamides Which are Sodium Channel Blockers", *J. Med. Chem.*, vol. 39, pp. 1514-1520 (1996).
C. Rundfeldt et al., "The novel anticonvulsant AWD 140-190 acts as a highly use-dependent sodium channel blecker in neuronal cell preparations", *Epilepsy Research*, vol. 34, pp. 57-64 (1999).
G. Schwartz et al., "Evaluation of the neuroprotective effects of sodium channel blockers after spinal cord injury: improved behavioral and neuroanatomical recovery with riluzole", *J. Neurosurg.*, 94(2), pp. 245-256 (2001). (Abstract Only).
S. Shanmuganathan et al., "Mitochondrial permeability transition pore as a target for cardioprotection in the human heart", *Am. J. Physiol Heart Circ Physiol*, vol. 289, pp. H237-H242 (2005).
F. Spadoni et al., "Lamotrigine derivatives and riluzole inhitir INa,P in cortical neurons", *Neuropharmacology and Neurotoxicology*, 13(9), pp. 1167-1170 (2002).
C.F. Starmer et al., "Proarrhythmic Response to Sodium Channel Blockade: Theoretical Model and Numerical Experiments", *Circulation*, 84(3), pp. 1364-1377 (1991).
A.G. Kanthasamy et al., "Effect of Riluzole on the Neurological and Neuropathological Changes in an Animal Model of Cardiac Arrest-Induced Movement Disorder", "The Journal of Pharmacology and Experimental Therapeutics", 288(3), pp. 1340-1348 (1999).
T. Koga et al., "The protective effects of CP-060S on ischaemia- and reperfusion-induced arrhythmias in anaesthetized rats", *British Journal of Pharmacology*, vol. 123, pp. 1409-1417 (1998).
B. Le Grand et al., "Late sodium current inhibition in human isolated cardiomyocytes by R 56865", *J. Cardiovasc Pharmacol.*, 31(5), pp. 800-804 (1998). (Abstract Only).
JX Liu et al., "Propafenone and disopyramide enhance post-ischemic contractile and metabolic recovery of perfused hearts", *Eur. J. Pharmacol.*, 250(3), pp. 361-369 (1993). (Abstract Only).
H. Matsumura et al., "Protective Effects of Ranolazine, a Novel Anti-ischemic Drug, on the Hydrogen Peroxide-Induced Derangements in Isolated, Perfused Rat Heart: Comparison with Dichloroacetate", *Japan. J. Pharmacol.*, vol. 77, pp. 31-39 (1998).
D.E. McBean et al., "Neuroprotective efficacy of lifarizine (RS-87476) in a simplified rat survival model of 2 vessel occlusion", *British Journal of Pharmacology*, vol. 116, pp. 3093-3098 (1995).
GV Naccarelli et al., "Carvedilol's antiarrhythmic properties: therapeutic implications in patients with left ventricular dysfunction", *Clin. Cardiol.*, 28(4), pp. 165-173 (2005). (Abstract Only).
WK Amery et al., "Lorcainide (R 15 889), a first review", *Acta Cardiol.*, 36(3), pp. 207-234 (1981). (Abstract Only).
H. Asanuma et al., "β-Adrenoceptor Blocker Carvedilol Provides Cardioprotection via an Adenosine-Dependent Mechanism in Ischemic Canine Hearts", *Circulation*, pp. 2773-2779 (2004).
GE Billman et al., "The calcium channel antagonist, flunarizine, protects against ventricular fibrillation", *Eur. J. Pharmacol.*, 212(2-3), pp. 231-235 (1992). (Abstract Only).
SC Black et al., "Effect of ranolazine on infarct size ina canine model of regional myocardial ischemia/reperfusion", *J. Cardiovasc. Pharmacol.*, 24(6), pp. 921-928 (1994). (Abstract Only).
H. Bonnemeier et al., "Carvedilol versus metoprolol in the acute phase of myocardial infarction", *Pacing Clin. Electrophysiol.*, 28(1), pp. S222-S226 (2005). (Abstract Only).

WA Catterall et al., "Molecular properties of brain sodium channels: an important target for anticonvulsant drugs", *Adv. Neural.*, vol. 79, pp. 441-456 (1999). (Abstract Only).
O. Fagbemi et al., "The effects of verapamil, prenylamine, flunarizine and cinnarizine on coronary artery occlusion-induced arrhythmias in anaesthetized rats", *Br. J. Pharmac.*, vol. 83, pp. 299-304 (1984).
G. Garthwaite et al., "Mechanisms of ischaemic damage to central white matter axons: A quantitative hitological analysis using rat optic nerve", *Neuroscience*, 94(4), pp. 1219-1230 (1999).
MB Gralinski et al., "Cardioprotective effects of ranolazine (RS-43285) in the isolated perfused rabbit heart", *Cardiovasc. Res.*, 28(8), pp. 1231-1237 (1994). (Abstract Only).
K. Inuo et al., "Cardioprotective Effect of Mexiletine in Acute Myocardial Ischemia—Studies in the Rabbit Closed Chest Ischemia Model", *Circulation Journal*, vol. 66, pp. 403-410 (2002).
T. Kamada et al., "Endoscopic observation of the gastric mucus in vivo stained with azure A", *Am. J. Gastroenterol.*, 65(6), pp. 532-538 (1976). (Abstract Only).
T. Kamiyama et al., "Effects of Aprindine on Ischemia/Reperfusion-Induced Cardiac Contractile Dysfunction of Perfused Rat Heart", *Japan J. Pharmacol.*, vol. 70, pp. 227-234 (1996).
FN Nasser et al., "Lidocaine-induced reduction in size of experimental myocardial infarction", *Am. J. Cardiol.*, 46(6), pp. 967-975 (1980). (Abstract Only).
M. Nakamura et al., "Antiarrhythmic effects of opitical isomers of disopyramide on canine ventricular arrhythmias", *J. Cardiovasc. Pharmacol.*, 27(3), pp. 368-375 (1996). (Abstract Only).
A. Stefani et al., "Differential inhibition by Riluzole, Lamotrigine, and Phenytoin of Sodium and Calcium Currents in Cortical Neurons: Implications for Neuroprotective Strategies", *Experimental Neurology*, vol. 147, pp. 115-122 (1997).
M.J. O'Neill et al., "Effects of $Ca^{2+}$ and $Na^+$ channel inhibitors in vitro and in global cerebral ischaemia in vivo", *European Journal of Pharmacology*, vol. 332, pp. 121-131 (1997).
XL Tian et al., "Mechanisms by which SCN5A mutation $N_{1325}S$ causes cardiac arrhythmias and sudden death in vivo", *Cardiovascular Research*, vol. 61, pp. 256-267 (2004).
YK Ju et al., "Effects of lignocaine and quinidine on th epersistent sodium current in rat ventricular myocytes", *Br. J. Phamacol.*, vol. 107, pp. 311-316 (1992).
F. Spadoni et al., "Lamotrigine derivatives and riluzole inhibit INa,P in cortical neurons", *Meuropharmacology and Neurotoxicology*, 13(9), pp. 1167-1170 (2002).
Becker, L.C. and G. Ambrosio, Myocardial Consequences of Reperfusion, Progress in Cardiovascular Diseases, Jul./Aug. 1987, pp. 23-44, vol. XXX, No. 1.
Bolli, R., Mechanism of Myocardial "Stunning", Circulation, 1990, pp. 723-738, vol. 82, Wolters Kluwer Health, Baltimore.
Brachfel, N., Characterization of the Ischemic Process by Regional Metabolism, The American Journal of Cardiology, Mar. 31, 1976, pp. 467-473, vol. 37, Cornell Medical Center, New York.
Braunwald E. and R.A. Kloner, The Stunned Myocardium: prolonged, postischemic ventricular dysfunction, Circulation, 1982, pp. 1146-1149, vol. 66, Wolters Kluwer Health, Baltimore.
Canero, E., et. al., Genesis of Arrhythmias and Mechanism of Electrical Defibrillation of the Heart, Bul Exp Biol, Jan. 1975, pp. 737-740, vol. 77, No. 7 (Abstract).
Chan, Aconite Poisoning, Clin Toxicol, Sep. 2009, pp. 279-285, vol. 47, No. 4, Philadelphia. (Abstract).
Deboer, L.W.V., et. al., A Flow- and Time-Dependent Index of Ischemic Injury After Experimental Coronary Occlusion and Reperfusion, Proceedings of the National Academy of Science USA, Sep. 1983, pp. 5784-5788, vol. 80.
Fox, K.A., et. al., Pathophysiology of Myocardial Reperfusion, Annual Reviews Med., 1985, pp. 125-144, vol. 36.
Harris, A.S., Delayed Development of ventricular Ectopic Rhythms Following Experimental Coronary Occlusion, Circulation, 1950, pp. 1318-1328, vol. 1, No. 13, Wolters Kluwer Health, Baltimore.
Jennings, R.B., et. al., Ischemic Tissue Injury, American Journal of Pathology, Oct. 1975, pp. 179-195, vol. 81, No. 1, Northwestern University, Chicago.

(56) References Cited

OTHER PUBLICATIONS

Jennings, R.B. and K.A. Reimer, Lethal Myocardial Ischemic Injury, American Journal of Pathology, Feb. 1981, pp. 241-255, vol. 102, No. 2.

Kloner, R.A. and E. Braunwald, Observations on Experimental Myocardial Ischaemia, Cardiovascular Research, 1980, pp. 371-395, vol. 14, Harvard Medical School, Boston.

Mestre, M., et. al., Frequency-independent Blockade of Cardiac Na+ Channels by Riluzole: Comarison with Established Anticonvulsants and Class I Anti-Arrhythmics, Fundam. Clin. Pharmacol:, 2000, pp. 107-117, vol. 14.

Murphy, M.L., et. al., Ventricular Performance and Biochemical Alteration of Regional Ischemic Myocardium After Reperfusion in the Pig, The American Journal of Cardiology, Oct. 1982, pp. 821-828, vol. 50.

Piper, et. al., Early Enzyme Release from Myocardial Cell Is Not Due to Irreversible Cell Damage, J Mol Cell Cardiol, 1984, pp. 385-388, vol. 16, Academic Press, London.

Przyklent, K. and RA Kloner, Superoxide Dismutase Plus Catalase Improve Contractile Function in the Canine Model of the "Stunned Myocardium", Circulation Research, 1986, pp. 148-156, vol. 58, Wolters Kluwer Health, Baltimore.

Sedlis, S.P., Mechanisms of Ventricular Arrhythmias in Acute Ischemia and Reperfusion, Cardiovasc. Clin., 1992, pp. 3-18, vol. 22, No. 1.

06774840.0, EP, Weiss.

Weiss S. M., et al., Riluzole reduces arrhythmlas and myocardial damage induced by coronary occlusion in anaesthetized pigs. Clinical and Experimental Pharmacology and Physiology, 2013, 40:856-863.

Barrett T. D., et al., Ischaemia selectivity confers efficacy for suppression of ischaemia-induced arrhythmias in rats. European Journal of Pharmacology; 2000, 398:365-374.

Campbell T. J., Subclassification of Class I Antlarrhythmic Drugs: Enhanced Relevance After CAST. Cardiovascular Drugs and Therapy; 1992, 6:519-528.

Milne J. R., et a., Class 1 antiarrhythmic drugs—Characteristic electrocardiographic differences when assessed by atrial and ventricular pacing. European Heart Journal; 1984, 5:99-107.

Morganroth J. and Goin J. E., Quinidine-related mortality in the short-to-medium-term treatment of ventricular arrhylhmies—A Meta-Analysis. Circulation; 1991, 84:1977-1983.

Ryan T. J. et al., ACC/AGA Guidelines for the Management of Patients with Acute Myocardial Infarction; Journal of the American College of Cardiology, 1996, 28(5):1328-1428 Please note due to the size of this publication, only relevant pp. 1328, 1329, 1330, 1331, 1332 and 1365 have been submitted.

Yadav A.V. and Zipes D. P., Prophylactic Lidocaine in Acute Myocardial Infarction: Resurface or Reburial? The American Journal of Cardiology; 2004, 94:606-608.

* cited by examiner

REDUCING MYOCARDIAL DAMAGE AND THE INCIDENCE OF ARRHYTHMIA ARISING FROM LOSS, REDUCTION OR INTERRUPTION IN CORONARY BLOOD FLOW

FIELD OF THE INVENTION

The present invention relates to a method and composition for reducing the extent of cell damage and/or cell death in mammalian hearts arising from one or more loss, reduction or interruption in the blood supply of one or more coronary arteries and/or coronary veins (such as may happen during a heart attack or during cardiac surgery or transplantation). The present invention further relates to a method and composition for reducing or eliminating the incidence of lethal and non-lethal cardiac arrhythmias from developing in mammalian hearts immediately (in terms of minutes and hours) subsequent to said one or more loss, reduction or interruptions in the blood supply of one or more coronary arteries and or coronary veins. The present invention yet further relates to a method and composition for reducing or eliminating the incidence of lethal and non-lethal cardiac arrhythmias from developing in mammalian hearts late (in terms of days, weeks, months and years) subsequent to said one or more loss, reduction or interruptions in the blood supply of one or more coronary arteries and/or coronary veins.

BRIEF DESCRIPTION OF THE ART

Loss, reduction or interruption in the blood supply to one or more arteries and/or one or more veins in the heart (coronary arteries and coronary veins), mainly in the form of heart attack, remains one of the biggest causes of death and heart disease in the western world. When a coronary artery or coronary vein is suddenly blocked by a blood clot or a spasm, or when blood flow through a coronary artery or vein is cut or slowed such as may happen during surgery and in particular coronary artery bypass surgery, the part of the heart muscle supplied with blood by that artery or drained of blood by that vein may become damaged or may die because of a starvation of blood (ischaemia). One component of the starvation of blood is a starvation of oxygen (hypoxia). Once heart muscle cells become hypoxic, a number of events may result, the outcome of these events possibly causing a decrease or cessation in the pumping of blood from the heart which in turn, could result in death of the patient.

While there are a number of current treatments available for a loss, reduction or interruption to blood flow in a coronary artery and/or vein or for a condition arising therefrom, there are no current treatments for heart muscle cell hypoxia—the focal event from which the other sequences of events mentioned above occur.

Given that death and heart disease from a loss, reduction or interruption in the blood supply to one or more coronary arteries and/or coronary veins remain prevalent despite the currently available treatments, it would be desirable to provide a treatment which reduces such death and disease. Moreover, it would be desirable to provide a treatment which could mitigate or even avert the events resulting from heart muscle cell hypoxia.

SUMMARY OF THE INVENTION

Surprisingly, it has been discovered in accordance with the present invention, that some pharmaceutical compositions for treating diseases of the brain and/or nervous system, each thought to reduce or inhibit persistent sodium currents and/or block a number of persistent sodium channels in mammalian neuronal cells, may be effective anti-arrhythmic agents for preventing or reducing the incidence of lethal and other mammalian cardiac arrhythmias, including automatic, triggered activity and re-entrant cardiac arrhythmias as well as single and multiple premature ventricular contractions/ectopic beats and bigeminy, trigeminy or any other single or multiple or alternating group of beats and/or any other sustained or non-sustained lethal or non-lethal cardiac arrhythmia from developing immediately (in terms of minutes and hours) subsequent to an hypoxic event and at similar concentrations to those used to treat said brain and/or nervous system diseases.

Moreover, it has surprisingly been discovered in accordance with the present invention, that some pharmaceutical compositions for treating diseases of the brain and/or nervous system, each thought to reduce or inhibit persistent sodium currents and/or block a number of persistent sodium channels in mammalian neuronal cells may be effective for limiting the extent of damage and/or death of mammalian cardiac cells within an hypoxic, ischaemic and/or infarcted region, and/or the size of the inside border of a border zone and/or the outside border of a border zone and/or the volume of a border zone of said mammalian cardiac cells developing as a result of an hypoxic event, and subsequently may be effective for enhancing cellular and haemodynamic recovery from such an hypoxic event and for providing cardio-protection from further hypoxic events at similar concentrations to those used to treat said brain and/or nervous system diseases.

Even further, it has surprisingly been discovered in accordance with the present invention, that some pharmaceutical compositions for treating diseases of the brain and/or nervous system, each thought to reduce or inhibit persistent sodium currents and/or block a number of persistent sodium channels of mammalian neuronal cells may be effective anti-arrhythmic agents for preventing or reducing the incidence of lethal and other mammalian cardiac arrhythmias, including automatic, triggered activity and re-entrant cardiac arrhythmias as well as single and multiple premature ventricular contractions/ectopic beats and bigeminy and trigeminy or any other single or multiple or alternating group of beats and/or any other sustained or non-sustained lethal or non-lethal cardiac arrhythmia, from developing late (in terms of days, weeks and months) after an hypoxic event but still developing as a result of that hypoxic event, at similar concentrations to those used to treat said brain and/or nervous system diseases. It has also surprisingly been discovered in accordance with the present invention that some pharmaceutical compositions for treating ischaemic cardiac arrhythmias, may be effective agents for preventing or reducing the incidence of lethal and other cardiac reperfusion arrhythmias, including automatic, triggered activity and re-entrant cardiac arrhythmias as well as single and multiple premature ventricular contractions/ectopic beats and bigeminy, trigeminy or any other single or multiple or alternating group of beats and/or any other sustained or non-sustained lethal or non-lethal cardiac arrhythmia from developing during or immediately subsequent to a reperfusion event.

Moreover, it has surprisingly been discovered in accordance with the present invention that some pharmaceutical compositions for treating ischaemic cardiac arrhythmias, may be effective for limiting the extent of damage and/or death of cardiac cells within an hypoxic, ischaemic and/or infarcted region, and/or the size of the inside border of a border zone and/or the outside border of a border zone and/or the volume of a border zone of said mammalian cardiac cells developing as a result of an hypoxic event, and subsequently may be effective for enhancing cellular and haemodynamic recovery from such an hypoxic event and for providing cardio-protection from further hypoxic events.

Accordingly, the present invention relates to a method and composition for preventing or reducing the extent of damage or death of cardiac cells and/or of reducing the size of the inside border, the outside border and/or the volume of a border zone and/or for aiding in cellular and haemodynamic recovery and/or cardio-protection, associated with hypoxia or a loss, reduction or interruption in blood flow to those cells, by systemically and/or directly administering to the heart of a mammal one or more pharmaceutical compositions which include one or more amounts of one or more persistent sodium channel blockers which are effective to block a number of persistent sodium channels of the cardiac cells of said mammal.

The present invention further relates to a method and composition for preventing or reducing the incidence of arrhythmias associated with hypoxia or a loss, reduction or interruption in blood flow to cardiac cells, by systemically and/or directly administering to the heart of a mammal one or more pharmaceutical compositions which include one or more amounts of one or more persistent sodium channel blockers which are effective to block a number of persistent sodium channels of the cardiac cells of said mammal.

More specifically, the present invention is directed to a method and composition for altering one or more possible sequences of pathological events in cardiac cells that may be associated with hypoxia or a loss, reduction or interruption in blood flow to those cardiac cells. The sequences include the pathological influx of sodium ions via persistent sodium channels and either the incidence of cardiac arrhythmias, and/or a subsequent reversal of the sodium/calcium exchanger and the incidence of cardiac arrhythmias, and/or the reversal of the sodium/calcium exchanger, a subsequent amount of damage and/or death to one or more cardiac cells including those in border zones with or without the incidence of cardiac arrhythmias.

Specifically, this blocking of a number of persistent sodium channels is achieved by administering to the cardiac cells one or more pharmaceutical compositions having one or more active ingredients with cardiac persistent sodium current or cardiac persistent sodium channel blocking activity.

Specific examples of persistent sodium channel blockers which could be used as the active effective ingredients in the pharmaceutical compositions of the present invention are described asralitoline, C1953, PD85639, lamotrigine, BW1003C87, BW619C89, fosphenytoin, zonisamide, riluzole, U-54494A, AWD-140-190, lifarizine, lomerizine, CNS 1237, benzothialzole, phenyl benzothialzole, GEA-968, azure A, pancuronium, and N-methylstrychnine.

An important facet of this invention is that persistent sodium channels in cardiac cells can be blocked without impacting upon the transient sodium channels which are critical for the normal functioning of the heart. It is to be understood that the term persistent sodium channel, as used here, relates to any channel which permits a persistent sodium current to pass through a cell membrane. As such, the terms blocking a persistent sodium current and blocking a persistent sodium channel, are synonymous as used here.

BRIEF DESCRIPTION OF THE DRAWINGS

The advantages and features of the present invention would be better understood by the following description when considered in conjunction with the accompanying drawings.

DETAILED DESCRIPTION OF THE INVENTION

Figure 1:
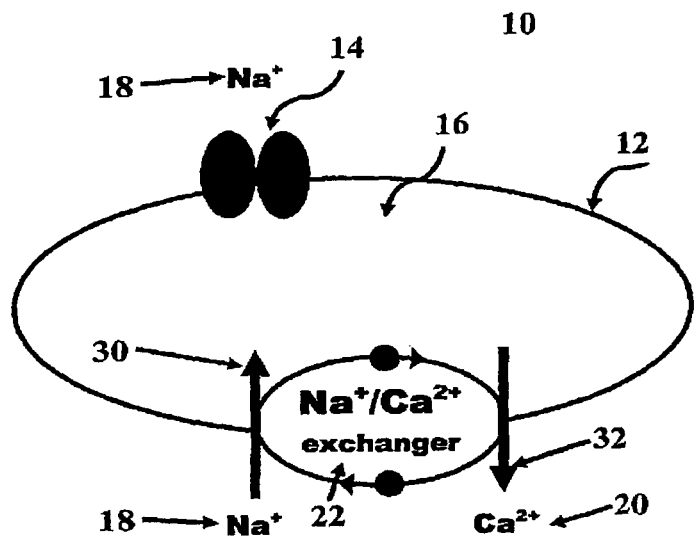
FIG. 1 shows a cardiac cell with a persistent sodium channel under normal conditions.

In a normally functioning heart, cells which contract do so in response to an electrical signal. This electrical signal depolarises each cell by raising the voltage inside the cell, which is normally resting at about −90 mV with respect to outside of the cell. As the cell depolarises, a threshold voltage is reached which causes pores through the membranous wall of the cell to open. The pores through the membrane are called channels and heart cells have many different types of channels which open and close to allow many different types of ions to pass or not pass through the membrane. Channels such as these which open when stimulated by an electrical signal, are called voltage-gated channels. When voltage-gated sodium channels are depolarised, sodium ions flow into the cell. This flow of sodium ions, called a sodium current, makes the voltage of the cell become positive.

Once a cell has depolarised, the voltage on that cell is sufficient to stimulate all of its adjacent cells to depolarise. Similarly, when those cells depolarise, they stimulate their adjacent cells to depolarise, and so on. However, once a cell has depolarised, it has to repolarise again before it is ready to receive another stimulus. Hence when a cell depolarises, a wave of depolarisation emanates and propagates through the heart muscle in all directions away from that first cell.

Before a cell can repolarise, the sodium channels have to inactivate (close) to stop any more sodium entering the cell. In traditional sodium channels, inactivation occurs within a few milliseconds of depolarisation. A number of different forms of voltage-gated sodium channels have been identified and are described by Catterall (Catterall W A (2000), From ionic currents to molecular mechanism: The structure and function of voltage-gated sodium channels, NEURON 26(1): 13-25). In addition to the multiple forms of sodium channel, there are possibly two types of sodium channel—the traditional transient sodium channel described by Hodgkin and Huxley (Hodgkin A L and Huxley A F (1952), A quantitative description of membrane current and its application to conduction and excitation in nerve, J Physiol, 117: 500-544) and the relatively recently identified persistent sodium channel (French C R and Gage P W (1985), A threshold sodium current in pyramidal cells in rat hippocampus, Neurosci Lett 56(3): 289-93).

Persistent sodium channels differ from transient sodium channels in that they remain open for several hundreds of milliseconds or longer as opposed to inactivating after just a few milliseconds. The persistent sodium current is only about 1 percent of the amplitude of the transient sodium current, however, because of the persistence of the channels remaining open, considerably more sodium can flow into the cells through each persistent sodium channel opening than through each transient sodium channel opening.

There are three hypotheses as to the mechanism behind persistent sodium currents a) that transient sodium channels and persistent sodium channels are different entities, b) that some transient sodium channels may gate in such a way as to permit a persistent sodium current to flow, and c) that some transient sodium channels may leak under certain conditions.

Irrespective of the mechanism underlying persistent sodium current manifestation, a number of deleterious physiological and pathological conditions have been attributed to this current. These include: retinal ganglion disease (Adorante J S, Ehring G R and Kopper K L, U.S. Pat. No. 6,479,458 November 2002), neuropathic pain (Yamamoto I, Itoh M, Yamasaki F, Akada Y, Miyazaki Y and Ogawa S, U.S. Pat. No. 6,642,257 November 2003 and Ehring Gr, Adorante J S, Donello J F, Wheeler L A and Malone T, US20050049287 March 2005), epilepsy (Ehring G R, Adorante J S, Wheeler L A, Malone T and Whitcup S M, U.S. Pat. No. 7,060,723 June 2006, and Ehring G R, Adorante J S, Wheeler L A, Malone T and Whitcup S M, US 20060154968 June 2006), atrial fibrillation (Beatch G N and Ezrin A M, Uses of ion channel modulating compounds US 20050026993 February 2005), convulsion (Hogenkamp D, Upasani R and Nguyen P, U.S. Pat. No. 6,737,418 May 2004), neurological ischaemia (Kobor J, Lazar L, Huber I et al., U.S. Pat. No. 5,494,909 February 1996), and cardiac arrhythmia (Yamamoto I, Itoh M, Yamasaki F, Miyazaki Y and Ogawa S, U.S. Pat. No. 6,710,060 March 2004). While some scientists hypothesise that blocking persistent sodium channels in cardiac cells treats cardiac arrhythmias, none have proven a relationship between blocking persistent sodium channels and a reduction in the incidence of cardiac arrhythmias and/or a reduction in the extent of myocardial damage or the consequences thereof. More-over, prior to the work of the present inventor, it had not been shown that persistent sodium channels in cardiac cells could be blocked without significantly impacting upon the transient sodium channels which are critical for the normal functioning of the heart, and reduce the incidence of cardiac arrhythmias and/or reduce the extent of myocardial damage, or the consequences thereof. Indeed, even though the existence of persistent sodium currents has been known for over 20 years, its relevance to treatment has been limited to various forms of neuronal conditions, and any research performed on cardiac tissue has been done on single cardiac cells which have not been involved in an arrhythmia.

There are a number of reasons why it was particularly surprising to discover that pharmaceutical compositions for treating neuronal diseases may be effective for preventing or reducing the incidence of cardiac arrhythmias and/or for limiting the extent of damage to cardiac cells from arising subsequent to an hypoxic event. The most obvious reason is that the function of the heart and the function of the cells in the heart, work very differently to the functions of the brain and nervous system and to neurons. While some pharmaceutical compositions have side effects on systems other than that of their primary action, these are usually not for the same action. For example, the pharmaceutical composition aspirin impacts the brain and nervous system to relieve pain. Aspirin, however, has a side effect on the cardiovascular system of thinning the blood. While the action of thinning the blood is most useful, it is clear that this action is quite different to that of relieving pain.

With regard to blocking persistent sodium channels, it was completely unexpected for a pharmaceutical composition intended for neuronal diseases to also block such channels in the heart. As stated by Yu and Catterrall (Yu F H and Catterall W A (2003), Genome Biol. 4(3): 207.1-207.7), "In addition to the differences in cellular and tissue expression, mammalian sodium channels also have differential expression profiles during development and different subcellular localizations, consistent with a distinct role for each channel in mammalian physiology." Yu and Catterrall further describe that while seven of the nine known isoforms of voltage-gated sodium channels, $Na_v1.1$, $Na_v1.2$, $Na_v1.3$, $Na_v1.6$, $Na_v1.7$, $Na_v1.8$, and $Na_v1.9$, are expressed in neuronal tissue, "$Na_v1.4$ and $Na_v1.5$ are muscle sodium channels that control the excitability of the skeletal and cardiac myocytes, respectively". Hence the role for the isoform of sodium channels in the heart ($Na_v1.5$) has a role distinct from the roles of the other isoforms of sodium channels.

The mechanism for blocking persistent sodium channels in the heart is also quite different to the mechanism for blocking persistent sodium channels in neurons as evidenced by the different concentrations of tetrodotoxin (TTX) required to block them. By definition, persistent sodium channels are channels which completely block with TTX. However the concentration of TTX required to block persistent sodium channels in heart cells is reportedly between 200 (Yu F H and Catterall W A (2003), Genome Biol. 4(3): 207.1-207.7) and 1000 (Aidley D J and Stanfield P R (1996), Ion Channels, Cambridge University Press, Great Britain, p. 238) times higher than the concentration required to block persistent sodium channels in the brain or nervous system. Indeed when TTX (also know as puffer fish toxin) is administered at doses required to block persistent sodium channels in the heart, it brings imminent death as it kills cells in the brain. Clearly, to have such a difference in response to TTX, the mechanism of action of persistent sodium channel blockade is different in the heart from that in the neuron. To-date, there has been no suggestion that pharmaceutical compositions exist which block persistent sodium channels in the heart at similar concentrations used to block persistent sodium channels in the brain or nervous system.

Using the methods disclosed in co-pending application AU2005905306, it has now been shown, as exemplified below, that persistent sodium channel blocking drugs reduce the incidence of many types of cardiac arrhythmias arising from hypoxia or a loss, reduction or interruption in coronary blood flow while additionally reducing the extent of myocardial damage caused by said hypoxia or loss, reduction or interruption.

With reference to Hammarstrom A K M and Gage P W (2002), Hypoxia and persistent sodium current, Eur Biophys J 31: 323-330, FIGS. 1 to 6 diagrammatically show a sequence of events at the cellular level. FIG. 1 shows a cardiac cell with cell wall 12, extracellular space 10, intracellular space 16, sodium ions 18 and calcium ions 20 in the extracellular space 10, a persistent sodium channel 14, a sodium/calcium exchanger 22 which under normal conditions pumps sodium ions 18 into the cell from the extracellular space 10 as shown at 30, and pumps calcium ions out of the cell into the extracellular space 10 as shown at 32. Under normal conditions, persistent sodium channel 14 is closed as shown.

Figure 2:
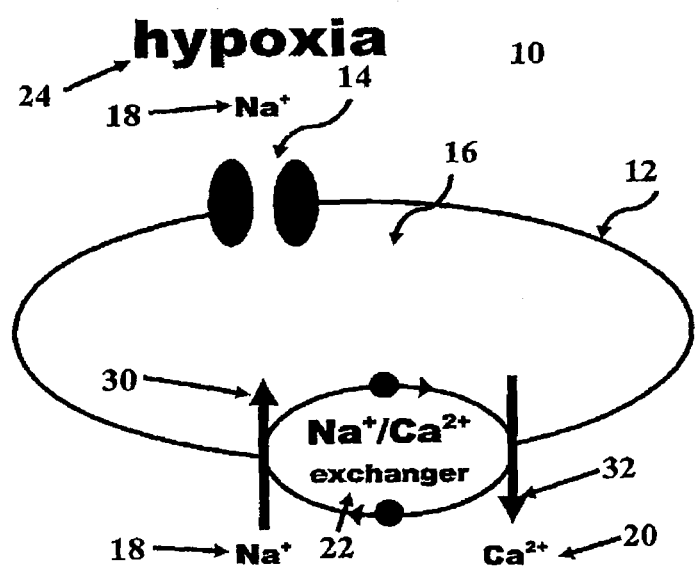
FIG. 2 shows a cardiac cell when the extracellular space becomes hypoxic and a persistent sodium channel opens.

During an event such as an acute myocardial infarction (heart attack), for example, an artery supplying a group of cardiac cells with blood becomes blocked so that blood no longer passes. When cardiac cells no longer receive blood because of such a blockage, the extracellular space becomes low in oxygen (hypoxic). When the extracellular space becomes hypoxic, persistent sodium channels open as shown in FIG. 2.

Figure 3:
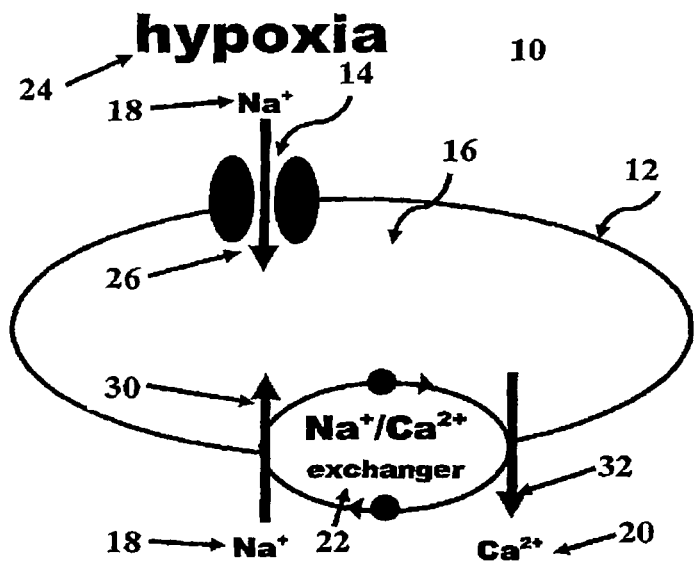
FIG. 3 shows the influx of sodium ions through the persistent sodium channel.

As persistent sodium channels 14 remain open for a relatively long period of time, they allow extracellular sodium ions 18 to enter the intracellular space 16 from the extracellular space 10 as shown at 26 in FIG. 3.

Figure 4:
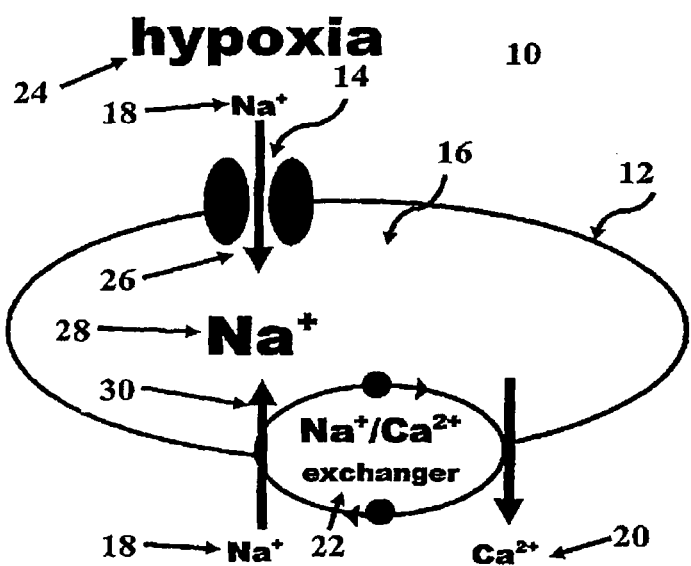
FIG. 4 shows the cardiac cell overloading with sodium ions.

With the persistent sodium channel 14 allowing sodium ions 18 into the cell 16 as shown at 26 while the sodium/calcium exchanger 22 pumps sodium ions 18 into the cell 16 as shown at 30, then the cell becomes overloaded with sodium ions as shown at 28 in FIG. 4.

Figure 5:
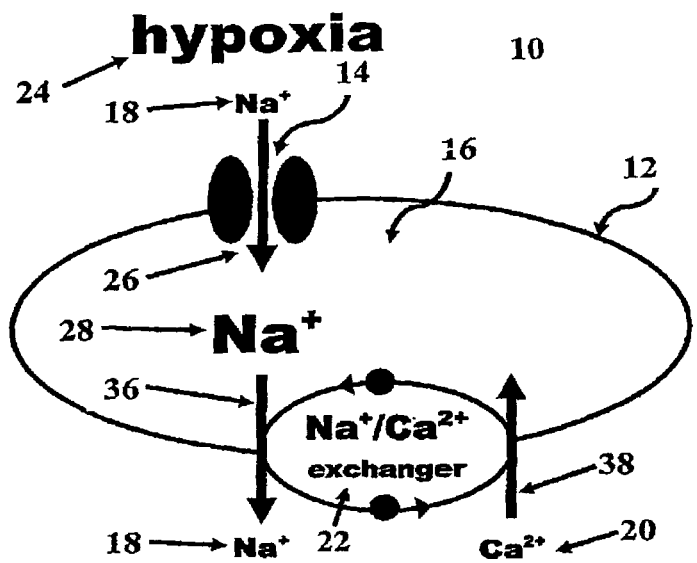
FIG. 5 shows the sodium/calcium ion exchanger reversing as a result of overloading the cell with sodium ions.

Overloading the intracellular space 16 with sodium ions 28 can cause the sodium/calcium exchanger 22 to reverse and pump sodium ions 28 out of the intracellular space 16 into the extracellular space 10 as shown at 36 in FIG. 5. Reversing the sodium/calcium exchanger simultaneously pumps calcium ions 20 into the intracellular space 16 as shown at 38 in FIG. 5.

Figure 6:
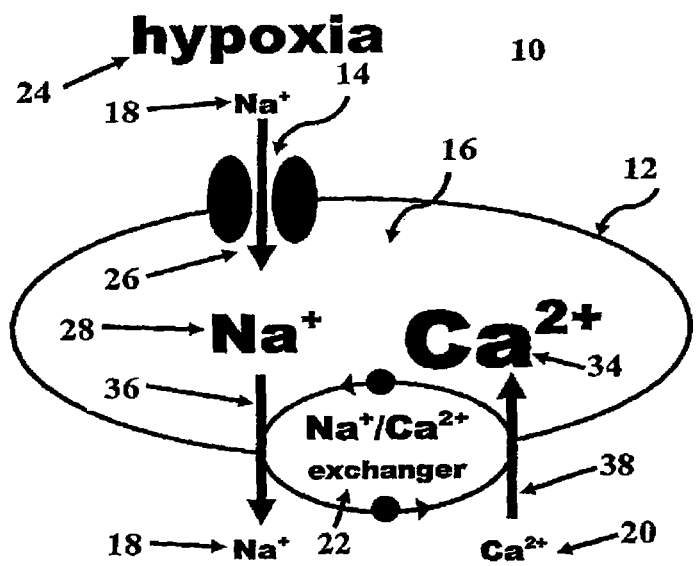
FIG. 6 shows the cardiac cell overloading with calcium ions as a result of the sodium/calcium ion exchanger reversing.

Finally, when the sodium/calcium exchanger 22 pumps calcium ions 20 into the intracellular space 16 as shown at 38, the intracellular space 16 becomes overloaded with calcium ions as shown at 34 in FIG. 6 thus damaging or killing the cells.

Figure 7:
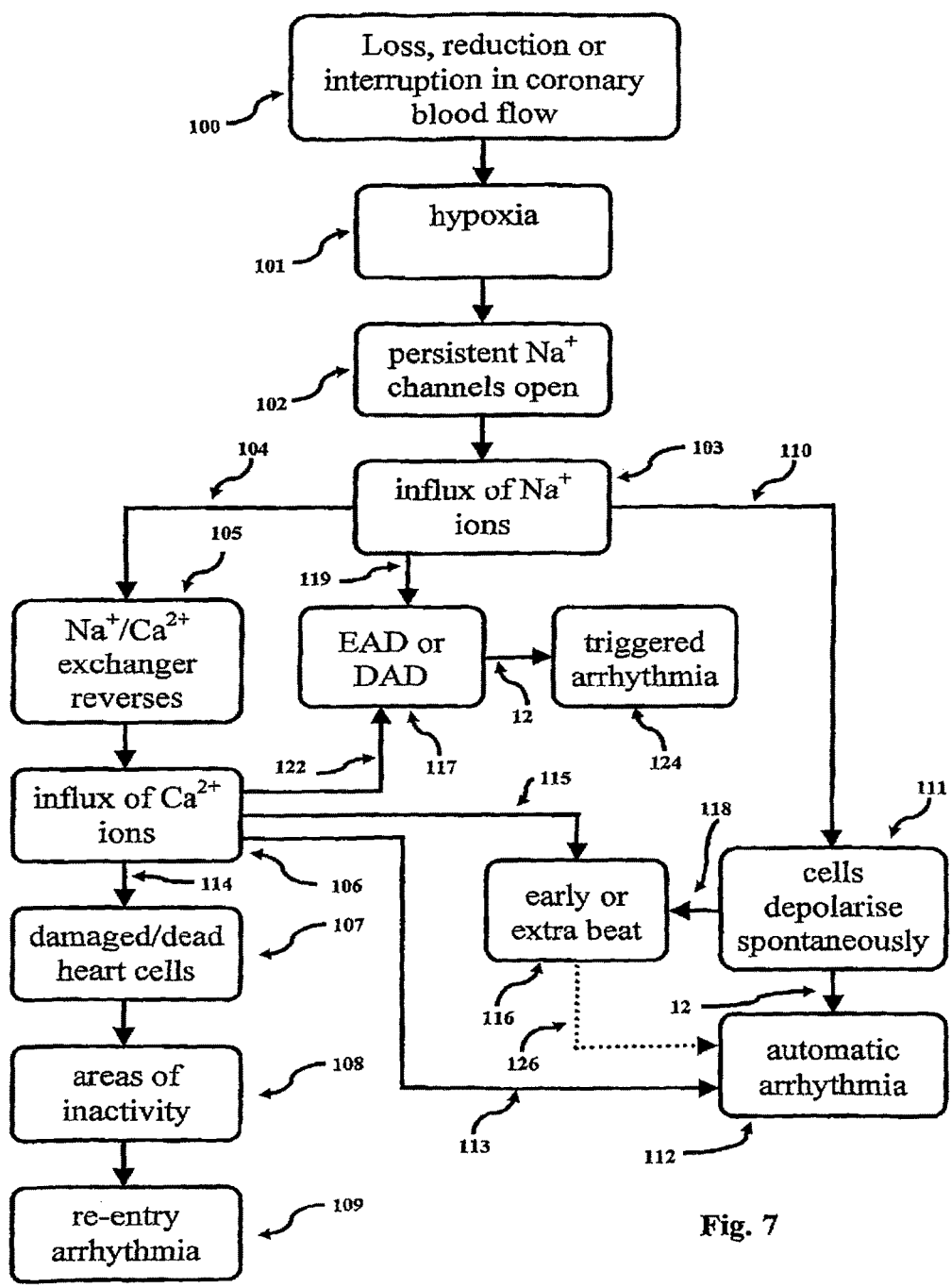
FIG. 7 shows a flowchart of several plausible sequences of events arising from hypoxia or the loss, reduction or interruption in coronary artery blood flow which result in lethal and/or potentially lethal arrhythmias and/or cardiac cell damage and/or cardiac cell death.

FIG. 7 shows seven plausible sequences of events, each of which can lead to lethal or non-lethal arrhythmias, one of which can also lead to significant haemodynamic compromise, and each sequence of events of which could be at least partially inhibited by the blockade of cardiac persistent sodium currents or channels. The sequences of events shown in FIG. 7 are the culmination of many sequences of individual cellular events as shown in FIGS. 1-6. The representation of many individual cellular events is required because arrhythmias cannot exist in isolated cells—they involve very many cardiac cells.

To understand FIG. 7, one must first understand some basic aspects of cardiac rhythms and arrhythmias (inappropriate rhythms). In a normally beating heart (normal rhythm), the electrical stimulus which causes the wave of depolarisation and contraction is started by pacemaker cells—a specialised group of cells which automatically depolarise and repolarise.

In an abnormally beating heart (arrhythmia), a wave or multiple waves of depolarisation and contraction are started in one or more inappropriate regions of the heart and by cells other than pacemaker cells. While the term arrhythmia can refer to slow heart rhythms (which, like normal rhythm, also originate in pacemaker cells), it usually refers to single and multiple premature ventricular contractions/ectopic beats, bigeminy and trigeminy, and in particular, to runs of multiple beats. Each beat in an arrhythmia occurs earlier than it should when compared with beats in normal rhythm and as such, the heart rate during an arrhythmia is faster than that during normal rhythm. This definition of arrhythmia is the one used in this document.

While slow rhythms can be treated with an artificial pacemaker, arrhythmias are much more difficult to control and can be so fast that the cardiac muscle doesn't have sufficient time to fully relax before receiving the next stimulus to contract. When this happens, the heart does not pump sufficient blood to the brain to sustain life and the animal or human dies within minutes unless the arrhythmia self-terminates or is terminated by external intervention such as by defibrillation.

There are predominantly three types of arrhythmias known as automatic arrhythmias, re-entry arrhythmias and triggered activity arrhythmias.

Automatic arrhythmias result from hyperactive cardiac cells which depolarise without receiving a stimulus from an adjacent cell, pacemaker cell or artificial pacemaker. When these hyperactive cells depolarise, they initiate a wave of depolarisation and subsequent wave of contraction which emanates from that cell. Thus if a hyperactive cell happens to be located toward the top of the ventricles, for example, the ensuing wave of contraction will be in a downwards direction away from the outlet of the ventricles and as such, the volume of blood ejected and the force of blood ejection from the ventricles will be lower than that from a properly beating heart.

Furthermore, in diseased heart muscle in particular, waves of depolarisation emanating from hyperactive cells often have to compete with normally generated waves of depolarisation for cells to depolarise (remembering that once a cell depolarises, it remains depolarised for a short length of time and can't be depolarised again until it first repolarises). As such, the shape of each wave-front travelling through the heart muscle can become highly irregular as it progresses from repolarised cell to repolarised cell. Given that such a wave-front cannot depolarise any cells which it comes across which are already in the depolarised state, the wave-front can fractionate to smaller wave-fronts and the situation can arise where the heart is subjected to multiple wave-fronts travelling seemingly randomly through the muscle. When this occurs, the heart muscle can be seen to have a number of regions of contraction at any one time—none of which produce effective blood pumping from the heart. Such a rhythm is called fibrillation and it is the fastest and most lethal of the arrhythmias.

Figure 8:
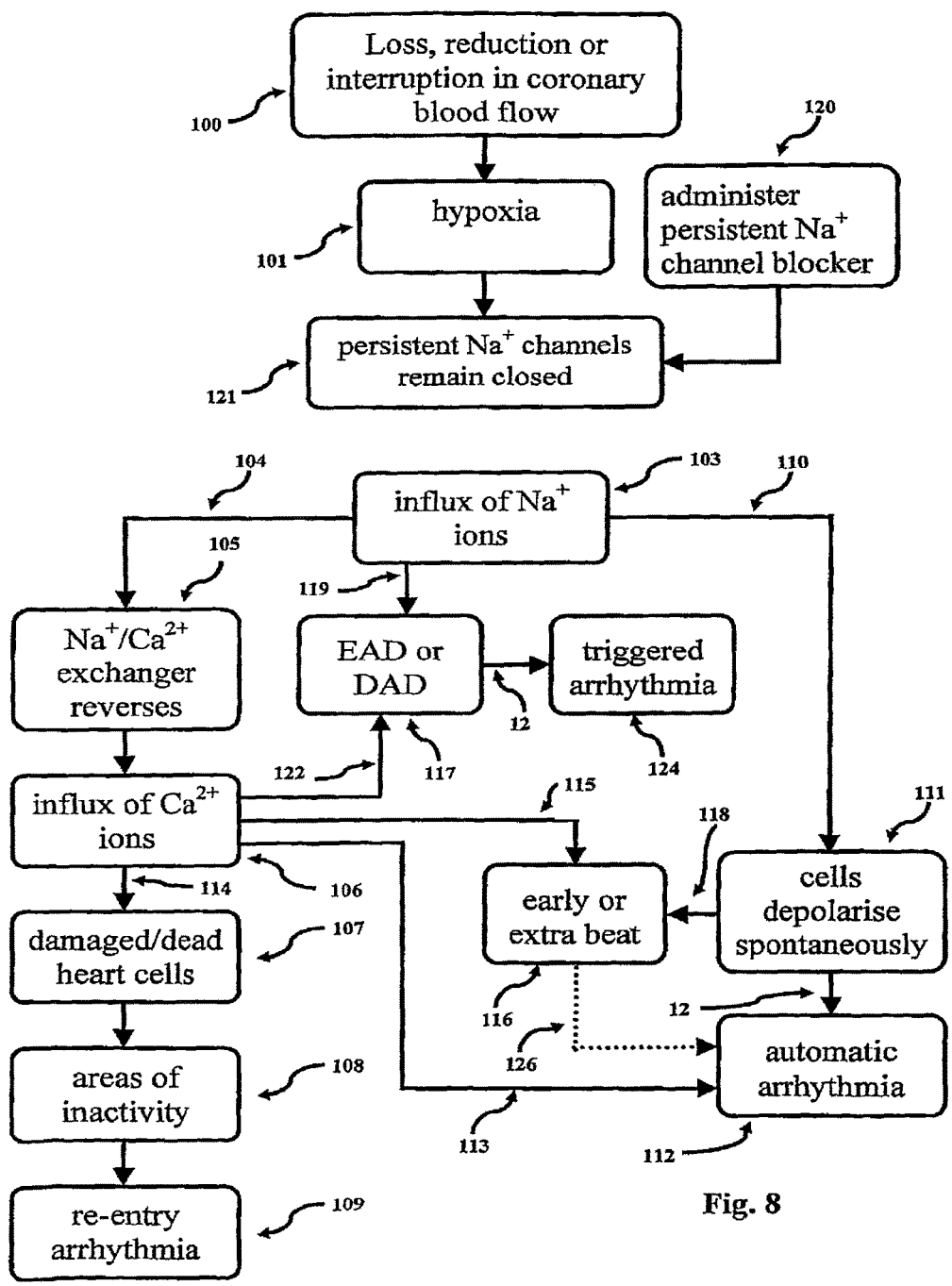
FIG. 8 shows the flowchart of FIG. 7 after the administration of a persistent sodium channel blocker.

As mentioned above, automatic arrhythmias result from spontaneous depolarisation of cardiac mile. As further mentioned above, depolarisation of cardiac cells involves an influx of ions across the cell membrane. It is known that an influx of sodium ions can cause cellular depolarisation. It is further known that an influx of calcium ions can cause cellular depolarisation. Thus a plausible sequence of events, as shown in FIG. 7 and involving the sequence of events as shown in FIGS. 1-6, comprises the steps of a loss, reduction or interruption in the flow of blood through one or more coronary vessels 100 in a mammalian heart leading to a loss, reduction or interruption of oxygen (hypoxia) 101 to a portion of that heart; said hypoxia 101 leading to the opening of persistent sodium channels 102 in the cell membranes of those hypoxic cells; the opening of said persistent sodium channels 102 leading to an influx of sodium ions 103 into those cells; the influx of sodium ions 103 leading via pathway 110 to a spontaneous depolarisation 111 of those cells which in turn results in an automatic arrhythmia 112 in the heart. As shown in FIG. 8, administering a composition 120 which blocks persistent sodium channels in cardiac cellular membranes and prevents the persistent sodium channels from opening 121, removes the link which would otherwise permit the influx of sodium ions 103 into those cells, the subsequent spontaneous depolarisation 111 of those cells and the subsequent automatic arrhythmia 112 in the heart. Hence in a first plausible sequence of events, the administration of the persistent sodium channel blocker 120 inhibits or prevents the genesis of automatic arrhythmias 112.

A second plausible sequence of events, as shown in FIG. 7 and involving the sequence of events as shown in FIGS. 1-6, comprises the steps of a loss, reduction or interruption in the flow of blood through one or more coronary vessels 100 in a mammalian heart leading to a loss, reduction or interruption of oxygen (hypoxia) 101 to a portion of that heart; said hypoxia 101 leading to the opening of persistent sodium channels 102 in the cell membranes of those hypoxic cells; the opening of said persistent sodium channels 102 leading to an influx of sodium ions 103 into those cells; the influx of sodium ions 103 leading via pathway 104 to a reversal of the sodium/calcium ion exchanger 105 in the wall of those cells; the reversal of the sodium/calcium ion exchanger 105 leading to an influx of calcium ions 106 into those cells which in turn results via pathway 113 in an automatic arrhythmia 112 in the heart. As shown in FIG. 8, administering a composition 120 which blocks persistent sodium channels in cardiac cellular membranes and prevents the persistent sodium channels from opening 121, removes the link which would otherwise permit the influx of sodium ions 103 into those cells, the subsequent reversal of the sodium/calcium exchanger 105, the influx of calcium ions 106 and the genesis of automatic arrhythmias 112 in the heart. Hence in a second plausible sequence of events, the administration of the persistent sodium channel blocker 120 inhibits or prevents the genesis of automatic arrhythmias 112.

A third plausible sequence of events, as shown in FIG. 7 and involving the sequence of events as shown in FIGS. 1-6, comprises the steps of a loss, reduction or interruption in the flow of blood through one or more coronary vessels 100 in a mammalian heart leading to a loss, reduction or interruption of oxygen (hypoxia) 101 to a portion of that heart; said hypoxia 101 leading to the opening of persistent sodium channels 102 in the cell membranes of those hypoxic cells; the opening of said persistent sodium channels 102 leading to an influx of sodium ions 103 into those cells; the influx of sodium ions 103 leading via pathway 110 to a spontaneous depolarisation 111 of those cells which in turn results via pathway 118 in one or more extra or early beats 116. While the extra or early beats are in themselves not lethal, they may be uncomfortable to a patient and furthermore, via pathway 126, may initiate an automatic arrhythmia 112 which could be lethal. As shown in FIG. 8, administering a composition 120 which blocks persistent sodium channels in cardiac cellular membranes and prevents the persistent sodium channels from opening 121, removes the link which would otherwise permit the influx of sodium ions 103 into those cells, the subsequent spontaneous depolarisation 111 and the genesis of extra or early beats 116 and possibly automatic arrhythmias 112 in the heart. Hence in a third plausible sequence of events, the administration of the persistent sodium channel blocker 120 inhibits or prevents the genesis of extra or early beats 116.

A fourth plausible sequence of events, as shown in FIG. 7 and involving the sequence of events as shown in FIGS. 1-6, comprises the steps of a loss, reduction or interruption in the flow of blood through one or more coronary vessels 100 in a mammalian heart leading to a loss, reduction or interruption of oxygen (hypoxia) 101 to a portion of that heart; said hypoxia 101 leading to the opening of persistent sodium channels 102 in the cell membranes of those hypoxic cells; the opening of said persistent sodium channels 102 leading to an influx of sodium ions 103 into those cells; the influx of sodium ions 103 leading via pathway 104 to a reversal of the sodium/calcium ion exchanger 105 in the wall of those cells; the reversal of the sodium/calcium ion exchanger 105 leading to an influx of calcium ions 106 into those cells which in turn results via pathway 115 in one or more extra or early beats 116. While the extra or early beats are in themselves not lethal, they may be uncomfortable to a patient and furthermore, via pathway 126, may initiate an automatic arrhythmia 112 which could be lethal. As shown in FIG. 8, administering a composition 120 which blocks persistent sodium channels in cardiac cellular membranes and prevents the persistent sodium channels from opening 121, removes the link which would otherwise permit the influx of sodium ions 103 into those cells, the subsequent reversal of the sodium/calcium exchanger 105, the influx of calcium ions 106 and the genesis of extra or early beats 116 and possibly automatic arrhythmias 112 in the heart. Hence in a fourth plausible sequence of events, the administration of the persistent sodium channel blocker 120 inhibits or prevents the genesis of extra or early beats 116.

Triggered activity arrhythmias are defined as the occurrence of non-driven action potentials that arise from afterdepolarisations that follow and are caused by previous action potentials (Kupersmith J (1993), Mechanisms of arrhythmia In: Clinical manual of electrophysiology, Williams & Wilkins USA). There are two types of afterdepolarisations, the early afterdepolarisation (EAD) which occurs during the repolarisation phase, and the delayed afterdepolarisation (DAD) which is a low amplitude oscillation occurring during diastole after repolarisation.

Afterdepolarisations are known to be associated with increases in intracellular calcium (Martian E, Robinson S W and Wier W G (1986), Mechanisms of arrhythmogenic delayed and early afterdepolarizations in ferret ventricular muscle, J Clin Invest 78(5): 1185-1192) and are thought to be associated with increases in intracellular sodium (Kupersmith J (1993), Mechanisms of arrhythmia In: Clinical manual of electrophysiology, Williams & Wilkins USA).

As such, a fifth plausible sequence of events, as shown in FIG. 7 and involving the sequence of events as shown in FIGS. 1-6, comprises the steps of a loss, reduction or interruption in the flow of blood through one or more coronary vessels 100 in a mammalian heart leading to a loss, reduction or interruption of oxygen (hypoxia) 101 to a portion of that heart; said hypoxia 101 leading to the opening of persistent sodium channels 102 in the cell membranes of those hypoxic cells; the opening of said persistent sodium channels 102 leading to an influx of sodium ions 103 into those cells; the influx of sodium ions 103 leading via pathway 119 to an EAD or a DAD 117 which in turn results via pathway 123 in a triggered activity arrhythmia 124. As shown in FIG. 8, administering a composition 120 which blocks persistent sodium channels in cardiac cellular membranes and prevents the persistent sodium channels from opening 121, removes the link which would otherwise permit the influx of sodium ions 103 into those cells, the subsequent occurrence of EADs or DADs 117 and the genesis of triggered activity arrhythmias 124. Hence in a fifth plausible sequence of events, the administration of the persistent sodium channel blocker 120 inhibits or prevents the genesis of EADs and/or DADs and possible subsequent triggered activity arrhythmias 124.

A sixth plausible sequence of events, as shown in FIG. 7 and involving the sequence of events as shown in FIGS. 1-6, comprises the steps of a loss, reduction or interruption in the flow of blood through one or more coronary vessels 100 in a mammalian heart leading to a loss, reduction or interruption of oxygen (hypoxia) 101 to a portion of that heart; said hypoxia 101 leading to the opening of persistent sodium channels 102 in the cell membranes of those hypoxic cells; the opening of said persistent sodium channels 102 leading to an influx of sodium ions 103 into those cells; the influx of sodium ions 103 leading via pathway 104 to a reversal of the sodium/calcium ion exchanger 105 in the wall of those cells; the reversal of the sodium/calcium ion exchanger 105 leading to an influx of calcium ions 106 into those cells which in turn leads to EADs or DADs 117 via pathway 122 and subsequently a triggered activity arrhythmia 124. As shown in FIG. 8, administering a composition 120 which blocks persistent sodium channels in cardiac cellular membranes and prevents the persistent sodium channels from opening 121, removes the link which would otherwise permit the influx of sodium ions 103 into those cells, the subsequent reversal of the sodium/calcium exchanger 105, the influx of calcium ions 106 and the genesis of EADs or DADs 117 and triggered activity arrhythmias 124 in the heart. Hence in a sixth plausible sequence of events, the administration of the persistent sodium channel blocker 120 inhibits or prevents the genesis of EADs and/or DADs and possible subsequent triggered activity arrhythmias 124.

In difference to automatic arrhythmias and triggered activity arrhythmias, re-entrant arrhythmias require the pathway for the wave of depolarisation to divide and propagate around an obstacle such as a region of damaged or dead cells which no longer depolarise and hence no longer conduct waves of depolarisation.

Subject to various criteria being met such as a slow forward conduction pathway, a fast backward conduction pathway and a forward conduction block in one of the pathways around the obstacle, when a wave-front of depolarisation propagating through normal heart cells reaches said divided pathway, the wave-front divides into two and continues to propagate on either side of the obstacle. At the site where one pathway is blocked to forward conduction, a propagating wave-front which has traveled around the obstacle will pass in a backward direction through the blockage. Provided that the conduction around the obstacle to the point of the block was sufficiently slow, the cells on the forward side of the blockage will have had sufficient time to repolarise and hence, when exposed to the wave-front travelling in the backward direction, will be ready to depolarise and hence conduct the wave-front in the backward direction around the obstacle.

Once the travelling wave-front reaches the forward end of the obstacle, the wave-front will continue to travel around and around the obstacle and, as the path length of the travelling wave-front around the obstacle is quite short, the cells in the path get depolarised much sooner than they would in a normally beating heart. Thus a re-entrant arrhythmia involves a path around an obstacle wherein a wave of depolarisation can continue to encircle and hence rapidly emanate waves of depolarisation through the heart muscle away from the obstacle.

Therefore, a seventh plausible sequence of events, as shown in FIG. 7 and involving the sequence of events as shown in FIGS. 1-6, comprises the steps of a loss, reduction or interruption in the flow of blood through one or more coronary vessels 100 in a mammalian heart leading to a loss, reduction or interruption of oxygen (hypoxia) 101 to a portion of that heart; said hypoxia 101 causing an opening of persistent sodium channels 102 in the cell membranes of those hypoxic cells; the opening of said persistent sodium channels 102 causing an influx of sodium ions 103 into those cells; the influx of sodium ions 103 causing via pathway 104 a reversal of the sodium/calcium ion exchanger 105 in the wall of those cells; the reversal of the sodium/calcium ion exchanger 105 causing an influx of calcium ions 106 into those cells; the influx of calcium ions 106 into cells via pathway 114 damaging or killing those cells 107 and causing areas of inactivity 108 which become the substrate for re-entrant arrhythmias 109. As shown in FIG. 8, administering a composition 120 which blocks persistent sodium channels in cardiac cellular membranes and prevents the persistent sodium channels from opening 121, removes the link which would otherwise permit the influx of sodium ions 103 into those cells, the subsequent reversal of the sodium/calcium exchanger 105, the influx of calcium ions 106, the damage and/or killing of the cells 107, the areas of inactivity 108, and the genesis of re-entrant arrhythmias 109 in the heart. Hence in a seventh plausible sequence of events, the administration of the persistent sodium channel blocker 120 inhibits or prevents the genesis of re-entrant arrhythmias 109.

It is most noteworthy in the seventh plausible sequence of events, as shown in FIG. 7, that the influx of calcium ions 106 into cells via pathway 114 can damage or kill those cells 107 and cause areas of inactivity 108. This second outcome from the seventh plausible sequence of events carries with it dire consequences, even in the absence of the development of re-entrant arrhythmias, as areas of inactivity in the heart can cause significant reduction in the efficiency of the pumping of the heart and in the cardiac output—the results of which could cause other medical conditions as well as a significant decrease in the patient's quality of life. Hence as shown in FIG. 8, administration of a persistent sodium channel blocker in the seventh plausible sequence of events 120 inhibits or prevents the damage and/or killing of those cells and the subsequent complications which may arise.

It is similarly important to note that cells which become damaged or which die as a result of hypoxia or a loss, reduction or interruption in the flow of blood through one or more coronary vessels, do so at different rates to each other. As such, hypoxic, ischaemic and infarcted regions of the heart will likely each comprise a combination of healthy, damaged and dead cells. Therefore a pharmaceutical composition which inhibits or prevents the damage or death of those cells could reduce the density of damaged tissue within an hypoxic, ischaemic or infarcted region of the heart.

It is further similarly important to note that many cells recover from the damage caused by hypoxia or a loss, reduction or interruption in the flow of blood through one or more coronary vessels, particularly after cardiac or coronary reperfusion. Therefore a pharmaceutical composition which reduces or prevents damage or death of those cells will likely enhance the cellular and haemodynamic recovery of the heart.

Yet further, it is important to note that when a pharmaceutical composition which inhibits or prevents the damage or death of those cells is administered in anticipation of an hypoxic or loss, reduction or interruption of coronary blood flow event such as in anticipation of an angioplasty event, it will likely provide cardio-protection against cellular damage and/or death which may arise from the hypoxic or loss, reduction or interruption of coronary blood flow event.

In addition to the above, and not shown in the Figures, is the concept of the border zone. The border zone is described by Nolan A C, Clark W A, Karwoski T and Zak R (1983) Proc Intl Nat Acad Sci USA 80: 6046-6050 as being composed of interdigitating ischemic and non-ischemic tissues.

The border zone is the zone of tissue surrounding, in three dimensions, an hypoxic, ischaemic or otherwise damaged region of tissue. The border zone in cardiac tissue is of particular clinical significance as many arrhythmias are considered to originate from within the zone (Kupersmith J (1993), Mechanisms of arrhythmia In: Clinical manual of electrophysiology, Williams & Wilkins USA). The border zone is also of clinical significance because a pharmaceutical composition which can cause the inside border of the border zone to infiltrate the damaged region, could reduce the volume of the damaged region to a volume smaller than that which is required to maintain a re-entrant circuit. Thus, decreasing the size of the inside border of a border zone could reduce or eliminate the incidence of re-entrant arrhythmias.

Furthermore, a consequence of reducing the size of the inside border of a border zone and hence reducing the extent of the damaged region, is a reduction in the volume of non-viable myocardium and hence a relative increase in the pumping efficiency of the heart.

Similarly, a pharmaceutical composition which can reduce the size of the outside border of the border zone can reduce the volume of the border zone and subsequently the opportunity for the tissue to initiate an arrhythmia. Thus reducing the size of the inside border of a border zone, the outside border of a border zone or reducing the volume of a border zone, could reduce the incidence of automatic arrhythmias, re-entrant arrhythmias, triggered activity arrhythmias, one or more beats in the form of any one or more of premature contractions, ectopic beats, bigeminy, trigeminy or any other single or multiple or alternating group of beats and/or any other sustained or non-sustained lethal or non-lethal cardiac arrhythmia.

Reducing the extent of cell damage and/or cell death either within one or more hypoxic, ischaemic and/or infarcted regions of the heart or within the border zones around such regions, reduces the density of damaged tissue in the heart. Reducing the density of damaged tissue in the heart reduces the opportunity and/or substrate for the generation of arrhythmias. Reducing the density of damaged tissue in the heart also reduces the deleterious effects such cell damage and/or cell death can have on the pumping efficiency of the heart, such as on any one or more of the various blood and intramuscular pressures created by or in the heart, or on such other haemodynamic parameters as myocardial contractility, cardiac output, blood flow, and even blood volume.

Furthermore, reducing the extent of cell damage and/or cell death increases the recovery from an hypoxic event both in terms of the time taken for the pumping efficiency of the heart to recover and in terms of the extent of recovery of haemodynamic function. Similarly, reducing the extent of cell damage and/or cell death reduces the time taken for many of those damaged cells to recover from the hypoxic event and regain functionality as well as reducing the number of damaged cells which subsequently die.

While a few damaged cells may spontaneously recover following a loss or reduction in coronary blood flow, many have the opportunity to recover following an interruption in coronary blood flow. One example of an interruption in coronary blood flow is cardiac artery bypass surgery. A more notable example, however, is the interruption which occurs during a heart attack which subsequently clears spontaneously or is cleared by medical intervention such as by coronary artery angioplasty. With early recognition of heart attacks becoming more prevalent, there is an increasing number of patients who survive an attack long enough to be admitted to hospital and to receive medical treatment to open or unblock one or more arteries following the attack. Hence the administration of a persistent sodium channel blocker to this patient group could not only reduce the incidence of arrhythmias, myocardial damage and haemodynamic compromise resulting from the loss or reduction in coronary blood flow, but could also reduce the incidence and/or extent of arrhythmias and/or myocardial damage and/or the degree of haemodynamic compromise resulting from the interruption of coronary blood flow.

Arrhythmias which occur during or following the opening of occluded or partially occluded coronary vessels are called reperfusion arrhythmias whereas those which occur as a result of a loss or reduction in coronary blood flow are called ischaemic arrhythmias. Similarly, myocardial and/or cell damage which occurs during or following the opening of occluded or partially occluded coronary vessels is called reperfusion injury whereas that which occurs as a result of a loss or reduction in coronary blood flow is called ischaemic injury.

While myocardial damage from an hypoxic event or a loss, reduction or interruption in coronary blood flow may compromise haemodynamic function, the skilled artisan will understand that an inherent property of arrhythmias is the compromise of haemodynamic function. Given that arrhythmias are heart beats which occur earlier in the cardiac cycle than the next normal beat would, then the time available for the heart chambers to fill with blood for pumping is shorter than normal and as such, the amount available for pumping and therefore the amount of blood pumped from the heart during an arrhythmia is less than that during normal rhythm. As such, haemodynamic function is compromised. Therefore, administration of a persistent sodium channel blocker which prevents or reduces the incidence of arrhythmias and/or converts sustained arrhythmias to non-sustained arrhythmias and/or shortens the duration of non-sustained arrhythmias and/or converts arrhythmias causing significant loss of haemodynamic function to arrhythmias causing less of a loss of haemodynamic function will inherently reduce the loss of haemodynamic function associated with said arrhythmia.

It is a key feature of the present invention to simultaneously treat any one or more of the plausible sequences of events described above which result in an arrhythmia, and treat the plausible damage and/or death of cardiac cells with the one step of blocking a number of persistent sodium currents or persistent sodium channels in cardiac tissue.

It is also a key feature of the present invention to reduce or eliminate the incidence of single and multiple premature ventricular contractions/ectopic beats, bigeminy, trigeminy and non-lethal arrhythmias as each of these can initiate or convert to a lethal arrhythmia.

It is further a key feature of the present invention to provide cardio-protection and a betterment in the quality of life of patients in each of the following patient groups—those at risk of a future hypoxic event, such as a heart attack; those undergoing medical intervention in the future, such as cardiac surgery; those who are having an hypoxic event or suspected hypoxic event at the time of persistent sodium channel blocker administration, such as in emergency care or coronary angioplasty; and those who have had an hypoxic event or suspected hypoxic event and -who are at risk of complications such as arrhythmias, myocardial damage, reperfusion arrhythmias and reperfusion injury developing from that hypoxic event and/or who are at risk of further hypoxic events.

The quality of life benefits from the administration of a persistent sodium channel blocker to any of the above patient groups are—psychological, in terms of the comfort a patient may gain from the knowledge that persistent sodium channel blockers will likely reduce or eliminate any damage or death to the heart cells arising from an hypoxic event; psychological, in terms of the comfort a patient may gain from the knowledge that persistent sodium channel blockers will likely reduce or eliminate the incidence of lethal and/or non-lethal arrhythmias and hence extend the patient's opportunity for survival from an hypoxic event; physiological, in terms of the likely reduction or elimination in the extent of damage or death of the heart cells and the subsequent impact on haemodynamic function; and physiological, in terms of the likely increase in survival due to a likely reduction or elimination in lethal and non-lethal arrhythmias developing from an hypoxic event.

As will readily be recognised by a person skilled in the art, the compounds utilised in accordance with the method of the present invention and in the compositions of the present invention may include a vehicle, preservatives, buffers, tonicity and pH adjusters, antioxidants and water provided that none of these additives have a deleterious or toxic effect on the heart or indeed on the patient.

Persistent sodium channel blocking agents, in accordance with the present invention, may be identified by the methods disclosed in the co-pending patent application Weiss SM, Apparatus and Method for Evaluating Cardiac Treatments (Australian Patent Application number 2005905306).

Specific examples of persistent sodium channel blockers which are used as the effective active ingredients of the present invention are described as ralitoline, C1953, PD85639, lamotrigine, BW1003C87, BW619C89, fosphenytoin, zonisamide, riluzole, U-54494A, AWD-140-190, lifarizine, lomerizine, CNS 1237, benzothialzole, phenyl benzothialzole, GEA-968, azure A, pancuronium, and N-methylstrychnine.

Riluzole (2-amino-6-tritluoromethoxybenzothiazole), for example, is described as a treatment for amyotrophic lateral sclerosis (ALS) (Louvel E, U.S. Pat. No. 5,527,814 June 1996), a disease unrelated to cardiac hypoxia, cardiac ischaemia, cardiac infarction, cardiac arrhythmias or cardiac function. Riluzole has also been found to be useful as an anticonvulsant, an anxiolytic and a hypnotic (Mizoule J, U.S. Pat. No. 4,370,338 January 1983), in the treatment of schizophrenia (Gueremy C, Maillard F and Musch B, U.S. Pat. No. 4,882,345 November 1989), in the treatment of sleep disorders and of depression (Blanchard J, Laduron P and Stutzmann J, U.S. Pat. No. 4,906,649 March 1990), in the treatment of cerebrovascular disorders and as an anaesthetic (Johnson G and Pavia M, U.S. Pat. No. 4,826,860 May 1989), in the treatment of spinal, cranial or cranio-spinal traumas (Rhone Poulenc Rorer, Doble A, Louvel E, Pratt J and Stutzmann J, WO9413288 June 1994), in the treatment of Parkinson's disease (Boireau A, Doble A, Dubedat P, Louvel E, Meunier M, Miquet J and Stutzmann J, U.S. Pat. No. 5,674,885 October 1997), and in the treatment of mitochondrial diseases (Delumeau J, Martinet M, Reibaud M and Stutzmann J, U.S. Pat. No. 5,686,475 November 1997). More recently, riluzole has been identified as a persistent sodium channel blocker for use in preventing optic nerve degeneration associated with glaucoma (Adorante J, U.S. Pat. No. 6,326,389 December 2001) and as a persistent sodium channel blocker in rat cortical neurons (Spadoni F, Hainsworth A H, Mercuri N B, Caputi L, Martella G, Lavaroni F, Bemardi G and Stefani A (2002), Lamotrigine derivatives and riluzole inhibit INa,P in cortical neurons, Neuroreport 13(9):1167-70).

As already described, even though riluzole may have persistent sodium channel blocking properties in neurons, it was surprising to learn that riluzole blocked cardiac persistent sodium channels and that it blocked such channels at similar concentrations to those used for blocking neuronal persistent sodium channels. Additionally, it was surprising to learn that riluzole blocked cardiac persistent sodium channels as it was previously thought to not have any antiarrhythmic properties (Mestre M, Djellas Y, Carriot T, Cavero I, (2000) Frequency-independent blockade of cardiac Na+ channels by riluzole: comparison with established anticonvulsants and class I anti-arrhythmics, Fundam Clin Pharmacol 14(2): 107-17) and as described in example 8 below, because riluzole did not significantly affect the electrocardiogram like normal sodium-channel blocking antiarrhythmic drugs do. As stated above, an important facet of this invention is that persistent sodium channels in cardiac cells can be blocked without impacting upon the transient sodium channels which are critical for the normal functioning of the heart. By blocking persistent sodium channels and yet not significantly affecting the electrocardiogram, the skilled addressee can readily recognise that riluzole has shown it possible to block persistent sodium channels in cardiac cells and get all the treatment benefits therefrom, without impacting upon the transient sodium channels critical for the normal functioning of the heart and more-over, without adversely impacting upon the transient sodium channels and placing the patient at risk of death.

Preparation of the compounds utilised in accordance with the method of the present invention and in the compositions of the present invention is based upon the delivery of an effective amount of active ingredient or ingredients to the heart cells depending upon the route of administration. Techniques for such preparation are known to those skilled in the art.

Administration of persistent sodium channel blockers to the heart cells may be achieved by any one or more of the following routes: intravenous administration; intracavitory administration directly into one or more chambers of the heart, oral administration in either a solid or a liquid form or a combination of both a solid and a liquid form; intramuscular administration either in skeletal muscle or directly into the heart muscle; topical administration either through the skin or directly applied onto the heart muscle; intra-pleural administration; intra-pericardial administration; intra-peritoneal administration; and/or inhalant administration. Persistent sodium channel blockers utilised in accordance with the present invention may be administered prophylactically prior to an expected hypoxic event (such as in a high risk patient group) or in instances of impending cardiac or coronary artery surgery, during an hypoxic event or a suspected hypoxic event such as an acute myocardial infarction, or following an hypoxic event or a suspected hypoxic event such as after an acute myocardial infarction or during coronary angioplasty.

Those skilled in the art will recognize that the frequency of administration depends on the precise nature of the active ingredient and its concentration in the formulation.

Example 1

In accordance with the method disclosed in the co-pending patent application entitled Apparatus and Method for Evaluating Cardiac Treatments (Australian Application number 2005905306), riluzole was evaluated in vivo for its effect on the incidence of single premature ventricular contractions (PVCs) subsequent to an hypoxic event. Pigs of either sex and weighing between 20 and 35 kg were each anaesthetised with thiopentone sodium (10-15 mg/kg iv) and maintained under general anaesthesia with isoflurane (0.5-2% in oxygen). Artificial ventilation was maintained at a volume of 15 ml/kg and a rate of 12 breaths per minute. Following connection of a lead II electrocardiogram and cannulation of the right femoral artery for blood pressure recordings, half of the animals were administered with riluzole ip (8 mg/kg). The remaining half of the animals served as a control group to which the riluzole results were compared. Subsequent to a mid-stemotomy and division of the pericardium, the left anterior coronary artery (LAD) was occluded mid-way along its length by permanent ligation.

During phase 1a (the first 15 minutes of hypoxia following LAD occlusion) and phase 1b (15-60 minutes post LAD occlusion), there was no significant difference in the number of spontaneous PVCs occurring in the control and riluzole groups. During phase 2 (60-180 minutes post LAD occlusion), however, the average number of PVCs dropped by 91% from 188 in the control group to 17 in the riluzole group.

Example 2

Using the method described above, riluzole was evaluated for its effect on multiple PVCs subsequent to an hypoxic event. As with single PVCs, there was no significant difference in the number of multiple PVCs occurring spontaneously in the control and riluzole groups during phases 1a and 1b. However, during phase 2, the average number of multiple PVCs dropped by 93% from 107 in the control group to 7 in the riluzole group.

Example 3

Using the method described above, riluzole was evaluated for its effect on geminy beats (bigeminy, trigeminy and quadrigeminy) subsequent to an hypoxic event. As with single and multiple PVCs, there was no significant in the number of multiple geminy beats occurring spontaneously in the control and riluzole groups during phases 1a and 1b. However, during phase 2, the average number of geminy beats dropped by 100% from 166 in the control group to 0 in the riluzole group.

Example 4

Using the method described above, riluzole was evaluated for its effect on non-sustained arrhythmias (defined in the study as episodes of ventricular tachycardia or ventricular fibrillation which spontaneously reverted to normal rhythm within 15 seconds of commencement) subsequent to an hypoxic event. These arrhythmias, while not being lethal because they spontaneously reverted to normal rhythm, are still of major concern because, for example, a patient may lose consciousness from a lack of blood supply to the brain as a result of the arrhythmia thus causing further injury if, for example, they were operating machinery at the time of the loss of consciousness. During phase 1a, the number of episodes of non-sustained arrhythmias fell by 43% from an average 0.30 episodes per animal in the control group to 0.17 episodes in the riluzole group. Similarly during phase 1b, the number of episodes of non-sustained arrhythmias fell by 35% from an average 3.60 episodes per animal in the control group to 2.33 episodes in the riluzole group. Far more significantly, during phase 2, the number of episodes of non-sustained arrhythmias fell by 92% from an average 8.60 episodes per animal in the control group to 0.67 episodes in the riluzole group.

Example 5

Using the method described above, riluzole was evaluated for its effect on sustained arrhythmias (defined in the study as episodes of ventricular tachycardia or ventricular fibrillation lasting for more than 15 seconds) subsequent to an hypoxic event. These arrhythmias would likely be lethal if not for external intervention in the form of cardioversion or defibrillation. During phase 1a, the number of episodes of sustained arrhythmias fell by 58% from an average 0.40 episodes per animal in the control group to 0.17 episodes in the riluzole group. An even better result was observed during phase 1b wherein the number of episodes of sustained arrhythmias fell by 86% from an average 2.30 episodes per animal in the control group to 0.33 episodes in the riluzole group. Even more significantly, during phase 2 the number of episodes of sustained arrhythmias fell by 90% from an average 3.40 episodes per animal in the control group to 0.33 episodes in the riluzole group. While there is no way of knowing how many, it is likely that riluzole caused some arrhythmias to revert to normal rhythm within the first 15 seconds of their commencement and hence to become non-sustained arrhythmias as demonstrated in Example 4.

Example 6

Using the method described above, riluzole was evaluated for its effect on the number of animals which developed non-sustained and sustained arrhythmias. In the control group, 90% of animals developed one or more episodes of non-sustained arrhythmias during the first three hours post commencement of hypoxia, and 100% of animals developed one or more episodes of sustained arrhythmias. In contrast, only 50% of animals in the riluzole group developed any non-sustained arrhythmias and similarly, only 50% developed any sustained arrhythmias.

Example 7

Using the method described above, riluzole was observed for its effect on the hypoxic region produced by coronary artery occlusion. The region of discolouration of the epicardial layer located toward the end of the ventricles distal to the coronary artery occlusion was notably smaller and less discoloured in the animals in the riluzole group as compared with those in the control group. These results suggest that riluzole decreased the extent of myocardial cellular damage and/or cellular death in at least the forms of hypoxia, ischaemia and infarction. These results further suggest that riluzole reduced the size of the inside border of the border zone around the hypoxic/ischaemic region of the heart which resulted from the LAD occlusion. These results further suggest that riluzole reduced the size of the outside border of the border zone.

Example 8

Using the method described above, riluzole was evaluated for its effect on the electrocardiogram when compared with the control group. ECGs were analysed continuously over the period from half an hour prior to coronary occlusion to three hours post occlusion. There were no significant differences in the R-R interval, P-R interval, QRS interval, QT interval or QTc intervals of the riluzole group when compared with the control group.

Thus pharmaceutical compositions according to the present invention, and in particular those including riluzole, may have cardiac antiarrhythmic properties, anti-ischaemic properties, cardio-protective properties, and properties which aid myocardial and haemodynamic recovery following a myocardial hypoxic event or a loss, reduction or interruption in coronary blood flow. More-over, pharmaceutical compositions according to the present invention, and in particular those including riluzole, may safely exert these properties without significantly impacting upon the transient sodium channels critical for the normal functioning of the heart as seen by a lack of significant difference in any three or more ECG intervals from the group: R-R interval, P-R interval, QRS interval and QTc interval, Therefore, in accordance with the above, the present invention includes one or more pharmaceutical compositions including one or more chemicals and/or compounds from the group: riluzole, ralitoline, C1953; PD85639, lamotrigine, BW1003C87, BW619C89, fosphenytoin, zonisamide, U-54494A, AWD-140-190, lifarizine, lomerizine, CNS 1237, benzothiazole, phenyl benzothiazole, GEA-968, azure A, pancuronium, and N-methylstrychnine or salts or derivatives thereof, when used individually or in combination to treat one or more myocardial arrhythmias and/or anticipated myocardial arrhythmias, including reperfusion arrhythmias, in a mammalian heart caused by a myocardial hypoxic event or a loss, reduction or interruption in coronary blood flow wherein the compositions treat the arrhythmias by blocking a number of persistent sodium channels in cell membranes of the heart.

The present invention further includes one or more pharmaceutical compositions including one or more chemicals and/or compounds from the group: riluzole, ralitoline, C1953, PD85639, lamotrigine, BW1003C87, BW619C89, fosphenytoin, zonisamide, U-54494A, AWD-140-190, lifarizine, lomerizine, CNS 1237, benzothiazole, phenyl benzothiazole, GEA-968, azure A, pancuronium, N-methylstrychnine, or salts or derivatives thereof, when used individually or in combination to treat myocardial damage and/or suspected myocardial damage and/or anticipated myocardial damage, including reperfusion injury, in a mammalian heart caused by a myocardial hypoxic event or a loss, reduction or interruption in coronary blood flow wherein the compositions treat the myocardial damage by blocking a number of persistent sodium channels in cell membranes of the heart.

The present invention also includes one or more pharmaceutical compositions for treating a sequence of pathological events or a suspected sequence of pathological events or an anticipated sequence of pathological events or a subsequent additional sequence of pathological events, said sequences of pathological events occurring in mammalian cardiac tissue and including a loss, reduction or interruption to the blood supply in one or more coronary arteries and/or coronary veins, and/or a loss, reduction or interruption to the blood supply in one or more regions of the heart and/or a loss, reduction or interruption to the oxygen supply to one or more parts of the one or more coronary arteries and/or coronary veins, and/or a loss, reduction or interruption to the oxygen supply to one or more regions of the heart, an onset of hypoxia, a cellular influx of sodium via one or more persistent sodium currents and/or persistent sodium channels, and the onset of myocardial arrhythmias and/or myocardial damage and/or cell death, wherein the pharmaceutical compositions include one or more chemicals and/or compounds from the group: riluzole, ralitoline, C1953, PD85639, lamotrigine, BW1003C87, BW619C89, fosphenytoin, zonisamide, U-54494A, AWD-140-190, lifarizine, lomerizine, CNS 1237, benzothiazole, phenyl benzothiazole, GEA-968, azure A, pancuronium, and N-methylstrychnine or salts or derivatives thereof, which when used individually or in combination reduce or inhibit the flow of persistent sodium current into mammalian cardiac cells or block a number of persistent sodium channels in mammalian cardiac cell membranes and wherein the composition treats the onset of myocardial arrhythmias and/or myocardial damage and/or cell death and/or converts sustained arrhythmias to non-sustained arrhythmias and/or shortens the duration of non-sustained arrhythmias and/or converts arrhythmias causing significant loss of haemodynamic function to arrhythmias causing less of a loss of haemodynamic function and/or reduces the volume and/or density of myocardial damage and/or cell death and/or reduces the extent of loss of haemodynamic function resulting from the myocardial damage in said mammalian cardiac tissue and/or reduces the size of the inside and/or outside borders and/or the volume of one or more border zones and/or reduces the size and/or density of myocardial damage within one or more border zones.

The present invention also includes a method for the treatment, amelioration or prevention of one or more myocardial arrhythmias and/or anticipated myocardial arrhythmias in a mammalian heart caused by a myocardial hypoxic event or a loss, reduction or interruption in coronary blood flow wherein the method involves the step of administering an effective amount of one or more pharmaceutical compositions including one or more chemicals and/or compounds from the group: riluzole, ralitoline, C1953, PD85639, lamotrigine, BW1003C87, BW619C89, fosphenytoin, zonisamide, U-54494A, AWD-140-190, lifarizine, lomerizine, CNS 1237, benzothiazole, phenyl benzothiazole, GEA-968, azure A, pancuronium, and N-methylstrychnine or salts or derivatives thereof and wherein the compositions treat, ameliorate or prevent the arrhythmias by blocking a number of persistent sodium channels in cell membranes of the heart.

The present invention further includes a method for the prophylactic treatment, amelioration or prevention of one or more anticipated myocardial reperfusion arrhythmias in a mammalian heart which may arise during or after coronary or cardiac reperfusion subsequent to a myocardial hypoxic event or a loss, reduction or interruption in coronary blood flow. The present invention also includes a method for the treatment, amelioration or prevention of myocardial damage and/or suspected myocardial damage and/or anticipated myocardial damage in a mammalian heart caused by a myocardial hypoxic event or a loss, reduction or interruption in coronary blood flow wherein the method involves the step of administering an effective amount of one or more pharmaceutical compositions including one or more chemicals and/or compounds from the group: riluzole, ralitoline, C1953, PD85639, lamotrigine, BW1003C87, BW619C89, fosphenytoin, zonisamide, U-54494A, AWD-140-190, lifarizine, lomerizine, CNS 1237, benzothiazole, phenyl benzothiazole, GEA-968, azure A, pancuronium, N-methylstrychnine or salts or derivatives thereof and wherein the compositions treat, ameliorate or prevent the myocardial damage by blocking a number of persistent sodium channels in cell membranes of the heart.

The present invention further includes a method for treating, ameliorating or preventing a sequence of pathological events or a suspected sequence of pathological events or an anticipated sequence of pathological events or a subsequent additional sequence of pathological events, said sequences of pathological events occurring in mammalian cardiac tissue and including a loss, reduction or interruption to the blood supply in one or more coronary arteries and/or coronary veins, and/or a loss, reduction or interruption to the blood supply in one or more regions of the heart and/or a loss, reduction or interruption to the oxygen supply to one or more parts of the one or more coronary arteries and/or coronary veins, and/or a loss, reduction or interruption to the oxygen supply to one or more regions of the heart, an onset of hypoxia, a cellular influx of sodium via one or more persistent sodium currents and/or persistent sodium channels, and the onset of myocardial arrhythmias and/or myocardial damage and/or cell death, wherein the method involves the step of administering to the mammal an effective amount of one or more pharmaceutical compositions which include one or more chemicals and/or compounds from the group: riluzole, ralitoline, C1953, PD85639, lamotrigine, BW1003C87, BW619C89, fosphenytoin, zonisamide, U-54494A, AWD-140-190, lifarizine, lomerizine, CNS 1237, benzothiazole, phenyl benzothiazole, GEA-968, azure A, pancuronium, and N-methylstrychnine or salts or derivatives thereof which when used individually or in combination reduce or inhibit the flow of persistent sodium current into mammalian cardiac cells or block a number of persistent sodium channels in mammalian cardiac cell membranes and in so-doing prevents the onset of myocardial arrhythmias and/or myocardial damage and/or cell death and/or converts sustained arrhythmias to non-sustained arrhythmias and/or shortens the duration of non-sustained arrhythmias and/or converts arrhythmias causing significant loss of haemodynamic function to arrhythmias causing less of a loss of haemodynamic function and/or reduces the volume and/or density of myocardial damage and/or cell death and/or reduces the extent of loss of haemodynamic function resulting from the myocardial damage in said mammalian cardiac tissue and/or reduces the size of the inside and/or outside borders and/or the volume of one or more border zones and/or reduces the size and/or density of myocardial damage within one or more border zones.

The present invention also includes methods for treating, ameliorating or preventing one or more arrhythmias and/or myocardial damage and/or cell death by the administration of said pharmaceutical compositions.

A key feature of the present invention is the simultaneous treatment, amelioration or prevention of one or more arrhythmias together with the treatment, amelioration or prevention of myocardial damage and/or myocardial cell death.

A further key feature of the present invention is the reduction in the overall size of the inside and/or outside border and/or the volume of one or more border zones and/or the reduction in the extent of non-viable myocardium and/or the overall density of damaged and/or dead tissue and/or the extent of the associated loss of haemodynamic function within the inside and/or outside borders and/or volume of one or more border zones and/or the prevention or reduction of the incidence of arrhythmias and/or conversion of sustained arrhythmias to non-sustained arrhythmias and/or the shortening of the duration of non-sustained arrhythmias and/or the conversion of arrhythmias causing significant loss of haemodynamic function to arrhythmias causing less of a loss of haemodynamic function when the arrhythmias originate in the one or more border zones around one or more hypoxic, ischaemic, infarcted and/or otherwise damaged or abnormal regions of the heart.

Another key feature of the present invention is that the blocking of the number of persistent sodium channels in the heart prevents or reduces the incidence of arrhythmias and/or converts sustained arrhythmias to non-sustained arrhythmias and/or shortens the duration of non-sustained arrhythmias and/or converts arrhythmias causing significant loss of haemodynamic function to arrhythmias causing less of a loss of haemodynamic function. Yet another key feature of the present invention is that the blocking of the number of persistent sodium channels in the heart prevents or reduces the incidence of myocardial damage and/or myocardial cell death and/or the blocking of the number of persistent sodium channels in the heart reduces the volume and/or the density of myocardial damage and/or, myocardial cell death and/or the blocking of the number of persistent sodium channels in the heart reduces the extent of loss of haemodynamic function resulting from the myocardial damage.

It is also a key feature of the present invention that the blockade of persistent sodium channels enhances the speed and extent of recovery of tissue and of haemodynamic function while also providing cardio-protection and preventing and reducing the incidence and extent of future cardiac arrhythmias and future myocardial damage and cell death as well as future loss of haemodynamic function. Another key feature of the present invention is that blockade of persistent sodium channels reduces the influx of sodium and thereby reduces a cellular influx of calcium and the subsequent development of one or more lethal and/or non-lethal cardiac arrhythmias and/or the development of myocardial damage and/or cellular death.

A further key feature of the invention is the ability of persistent sodium channel blockade to avert a decrease in quality of life by providing cardio-protection and preventing and/or reducing the incidence and/or extent of cardiac arrhythmias and/or myocardial damage and/or cell death and/or loss of haemodynamic function.

Yet a further key feature of the present invention is that persistent sodium channel blockade prevents and/or reduces the incidence and extent of arrhythmias and/or myocardial damage and/or cell death from occurring during or after myocardial reperfusion.

Another key feature of the present invention is that the above-mentioned mammalian heart is human.

Yet another key feature of the present invention is that the chemicals and/or compounds of the invention are administered at doses similar to or lower than those recommended for their primary action.

A feature of the present invention is that the pharmaceutical compositions treat myocardial disorders in a mammalian heart by enhancing the recovery of tissue and/or haemodynamic function subsequent to a myocardial hypoxic event or a loss, reduction or interruption in coronary blood flow or a coronary or myocardial reperfusion event.

Another feature of the present invention is that the pharmaceutical compositions treat myocardial disorders in a mammalian heart by conferring cardio-protective properties to protect the heart by inhibiting or reducing the incidence of future cardiac reperfusion rhythm disorders and/or by inhibiting or reducing the incidence of future myocardial damage disorders and/or by reducing the extent of future myocardial damage disorders and/or by reducing the incidence or extent of future haemodynamic disorders which may arise from a myocardial hypoxic event or a loss, reduction or interruption in coronary blood flow.

A further feature of the present invention is that the pharmaceutical compositions reduce the extent of myocardial damage by reducing the overall volume and/or by reducing the overall density of damaged tissue within the damaged region or regions.

It is to be understood that myocardial arrhythmias and/or myocardial damage and/or cell death according to the present invention could occur in the atrial and/or ventricular and/or supra-ventricular and/or outflow tract regions of the heart.

It is to be understood that the arrhythmias treated by the present invention include arrhythmias from the group: automatic arrhythmias, re-entrant arrhythmias, triggered activity arrhythmias, one or more beats in the form of any one or more of premature contractions, ectopic beats, bigeminy, trigeminy or any other single or multiple or alternating group of beats and/or any other sustained or non-sustained lethal or non-lethal cardiac arrhythmia.

It is also to be understood that myocardial damage and/or cell death treated by the present invention includes damage and/or cellular death from the group: hypoxia, ischaemia, infarction, necrosis, reperfusion injury, myopathy, hypertrophy, inflammation, scarring or any other form of alteration to the normal function of the cardiac cells or tissue.

It is to be understood that pharmaceutical compositions according to the present invention may be administered to the mammal by any one or more of the routes from the group: orally, sublingually, nasally, intravenously, intracavitorily directly into one or more chambers of the heart, intra-muscularly, intra-myocardially, topically to any surface including the epicardium, endocardium, pericardium, skeletal muscle and skin, intraperitoneally, intrapleurally, intrapericardially, and/or subcutaneously.

In addition, pharmaceutical compositions according to the present invention may be administered to the mammal via one or more devices from the group: biodegradable implantable drug-eluting devices, non-biodegradable implantable drug-eluting devices, implantable drug pumps.

It is even further to be understood that pharmaceutical compositions according to the present invention may be administered to the mammal in multiple doses via a single route or in multiple doses via different routes.

A further feature of the present invention is that the one or more pharmaceutical compositions have at least a 10-fold selectivity or preferably at least a 20-fold selectivity or more preferably at least a 50-fold selectivity or even more preferably at least a 100-fold selectivity for persistent sodium currents or persistent sodium channels relative to transient sodium currents or transient sodium channels.

Another key feature of the present invention is that the one or more pharmaceutical compositions can reduce or avert a decrease in quality of life by reducing the size of the inside and/or outside borders of the border zone and/or the volume of said border zone and/or the extent of non-viable myocardium in the heart and/or the overall density of damaged tissue within the border zone.

It is to be understood that the scope of the invention is not limited to the disclosures of the examples or of the attached drawings and associated descriptions as these disclosures are merely examples of several aspects of the workings of the invention. It is also to be understood that the skilled artisan will readily recognise that the blocking of the persistent sodium current, as described in this invention, is synonymous with the blocking of persistent sodium channels. It is further to be understood that the skilled artisan will readily recognise that the blocking of multiple persistent sodium channels is not an all-or-none phenomenon and therefore that different doses of persistent sodium channel blockers will block different numbers of persistent sodium channels.

The skilled artisan will readily recognise that the dose of persistent sodium channel blocker required to block an appropriate number of persistent sodium channels in order to carry out the invention can be determined by simple trial and error.

Specifically, the present invention is drawn to 1. a pharmaceutical composition when used in the treatment of a myocardial disorder of the type arising from a persistent sodium current influx in cardiac cells in a human heart when the persistent sodium current influx is caused by a 15 minute or longer hypoxic event, wherein the composition includes as its active ingredient a persistent sodium current blocker, and further wherein an effective amount of the pharmaceutical composition at least partially blocks persistent sodium channels in the cardiac cells without impacting upon the transient sodium channels critical for the normal functioning of the heart, 2. a pharmaceutical composition when used in the treatment of a myocardial disorder of the type arising from a persistent sodium current influx in cardiac cells in a human heart when the persistent sodium current influx is caused by a 15 minute or longer hypoxic event, wherein the composition includes as its active ingredient at least one persistent sodium current blocker, and wherein an effective amount of the pharmaceutical composition at least partially blocks the persistent sodium current influx in the cardiac cells without causing a significant difference in any three or more ECG intervals from the group: R-R interval, P-R interval, ORS interval and QTc interval, 3. a pharmaceutical composition when used for treating a sequence of pathological events, said sequence of pathological events occurring in a mammalian heart and including a reduction in blood flow in at least one region of the heart, said reduction in blood flow lasting for at least 15 minutes, said reduction in blood flow producing hypoxia in the at least one region of the heart, said hypoxia producing a cellular influx of sodium via one or more persistent sodium channels in the at least one region of the heart, said influx of sodium overloading the cells in the at least one region of the heart with sodium, wherein the pharmaceutical composition treats the cellular influx of sodium and the sodium overload by at least partially blocking the persistent sodium current influx in the cardiac cells without causing a significant difference in any three or more ECG intervals from the group: R-R interval, P-R interval, QRS interval and QTc interval, 4. a method for treating myocardial damage in a myocardial disorder of the type arising from a persistent sodium current influx in cardiac cells in a human heart when the persistent sodium current influx is caused by a 15 minute or longer hypoxic event, wherein the method includes the step of administering to the heart the effective amount of the pharmaceutical composition of item 2 above, 5. and a method for treating a sequence of pathological events, said sequence of pathological events occurring in a mammalian heart and including a reduction in blood flow in at least one region of the heart, said reduction in blood flow lasting for at, least 15 minutes, said reduction in blood flow producing hypoxia in the at least one region of the heart, said hypoxia producing a cellular influx of sodium via one or more persistent sodium channels in the at least one region of the heart, said influx of sodium overloading the cells in the at least one region of the heart with sodium, wherein the method includes the step of administering to the heart an effective amount of the pharmaceutical composition of item 3 above, and wherein the pharmaceutical composition includes riluzole or one of its pharmaceutical salts.

As used herein: the term "hypoxia" refers to a deficiency of oxygen reaching the tissues of the body; the term "hypoxic event" refers to any event which causes hypoxia; the term "myocardial damage" refers to any damage to the myocardium which impairs function or structure; the term "ischaemia" refers to a deficiency of blood supply to a tissue or organ; the term "myocardial ischaemic event" refers to any event which causes ischaemia in the heart or part thereof, the term "ischaemic myocardial arrhythmia" refers to arrhythmia caused by a myocardial ischaemic event; the term "reperfusion" refers to restoration of the flow of blood to a previously ischaemic tissue or organ; the term "reperfusion injury" refers to myocardial damage caused by reperfusion; and the term "reperfusion arrhythmia" refers to arrhythmia caused by reperfusion.

The invention claimed is:

1. A method of reducing the incidence of cardiac arrhythmia following the onset of myocardial ischemia, said method comprising administering to a patient in need thereof a pharmaceutical composition comprising a therapeutically effective amount of riluzole or a pharmaceutically acceptable salt thereof concomitant with or immediately prior to the onset of the myocardial ischemia, wherein said administration reduces the incidence of cardiac arrhythmia for up to 180 minutes following the onset of the myocardial ischemia.

2. The method of claim 1 wherein administration of the pharmaceutical composition comprising a therapeutically effective amount of riluzole or pharmaceutically acceptable salt thereof provides a therapeutically effective amount of riluzole in the patient's blood.

3. The method of claim 2 wherein the pharmaceutical composition comprising a therapeutically effective amount of riluzole or a pharmaceutically acceptable salt thereof is administered immediately prior to the onset of the myocardial ischemia.

4. The method of claim 1 wherein administering the pharmaceutical composition is performed using one or more routes of administration selected from the group consisting of: orally, sublingually, nasally, intravenously, intracavitorily directly into one or more chambers of the heart, intramuscularly, intra-myocardially, topically to any surface including the epicardium, endocardium, pericardium, skeletal muscle and skin, intraperitoneally, intrapleurally, intrapericardially, and/or subcutaneously, and further wherein the administration may be performed via one or more devices selected from the group consisting of: biodegradable implantable drug-eluting devices, non-biodegradable implantable drug-eluting devices, and implantable drug pumps.

5. The method of claim 1 wherein administering the pharmaceutical composition blocks persistent sodium channels in myocardial cells of the patient.

6. The method of claim 5 wherein the pharmaceutical composition blocks the persistent sodium channels without causing a significant difference in any three or more intervals selected from the group consisting of: the R-R interval, the P-R interval, the QRS interval and the QTc interval.

7. The method of claim 1 wherein the myocardial ischemia further compromises the pumping of blood from the heart of the patient and wherein the method additionally reduces the level of compromise.

* * * * *